(12) United States Patent
Yu et al.

(10) Patent No.: US 6,380,187 B2
(45) Date of Patent: *Apr. 30, 2002

(54) CLASS OF THIOMORPHOLINO SUBSTITUTED THIAZOLES

(76) Inventors: Dingwei Tim Yu, 210 Frost Hollow Rd., Easton, PA (US) 18040; Orest Taras Macina, 3792-B Logans Ferry Rd., Pittsburgh, PA (US) 15239; Ila Sircar; Jagadish Chandra Sircar, both of 102 Skyline Dr. North, Clarks Summit, PA (US) 18411; Christopher Mark Riviello, 104 Cherokee La., Old Forge, PA (US) 18518

( * ) Notice: Subject to any disclaimer, the term of this patent is extended or adjusted under 35 U.S.C. 154(b) by 0 days.

This patent is subject to a terminal disclaimer.

(21) Appl. No.: 09/730,015

(22) Filed: Dec. 5, 2000

Related U.S. Application Data

(62) Division of application No. 09/275,863, filed on Mar. 25, 1999, now Pat. No. 6,156,776.

(51) Int. Cl.[7] ..................... C07D 417/10; A61K 31/541
(52) U.S. Cl. ........................................ 514/227.8; 544/60
(58) Field of Search ........................... 544/60; 514/227.8

(56) References Cited

U.S. PATENT DOCUMENTS

| | | | |
|---|---|---|---|
| 2,852,385 A | 9/1958 | Jones | 96/104 |
| 3,189,447 A | 6/1965 | Neugebaner et al. | 96/1 |
| 3,989,690 A | * 11/1976 | Verge et al. | 260/240 |
| 4,346,157 A | 8/1982 | Kakuta et al. | 430/586 |
| 4,746,669 A | 5/1988 | Caldwell et al. | 514/342 |
| 5,342,851 A | 8/1994 | Sanfilippo et al. | 514/370 |
| 5,474,995 A | 12/1995 | Ducharme et al. | 514/241 |

FOREIGN PATENT DOCUMENTS

| | | | |
|---|---|---|---|
| FR | 1291580 | 2/1961 | 120/167 |

* cited by examiner

*Primary Examiner*—Laura L. Stockton
(74) *Attorney, Agent, or Firm*—Joseph W. Molasky & Associates; Joseph W. Molasky

(57) ABSTRACT

Disclosed is a novel class of thiazole, thiadiazole, and oxadiazole compounds which are substituted at their nuclear carbons by aromatic moieties. These compounds exhibit antifungal activity against a variety of fungi including strains which have proven to be resistant to treatment with known antifungal agents such as Fluconazole.

5 Claims, No Drawings

CLASS OF THIOMORPHOLINO SUBSTITUTED THIAZOLES

This is a divisional of application Ser. No. 09/275,863 filed on Mar. 25, 1999 now U.S. Pat. No. 6,156,776.

This invention relates to a novel class of substituted azoles and, more specifically, diaryl substituted thiazoles, diaryl substituted thiadiazoles and diaryl substituted oxadiazoles, compounds which are useful in the treatment of fungal infections in mammals including humans. These compounds are active against a broad spectrum of fungi such as *Candida albicans, Candida parpsilosis, Candida tropicalis, Candida Krusei, Cryptococcus neoformans, Aspergillus fumigatus* and *Torulopsis glabrata*. Moreover, compounds within this series are also active against Fluconazole resistant strains and isolates.

BACKGROUND OF THE INVENTION

Opportunistic fungal infections are responsible for increased morbidity and mortality among patients suffering from AIDS and other immunocompromised diseases including infections resulting from neutropenia, cancer chemotherapy and organ transplantation (Annals N.Y. Acad. Sc., 544:1–3).

Moreover, until recently, the treatment of deep seated fungal infections has lagged behind the treatment of bacterial infections and only a few systemic agents are available for combatting these invasive pathogens.

Current therapy provides for administering polyenes such as amphotericin B, allylamines such as Naftafin and Terbinafin and azoles such as Fluconazole, Itraconazole and Ketoconazole. Amphotericin B, once the treatment of choice, is no longer favored due to the acute and chronic toxicities associated with its use.

Also, antifungal azoles are fungistatic, not fungicidal, and this has resulted in azole resistant fungi, that is, fungi strains and isolates which are resistant to treatment with Fluconazole and other known antifungal agents (New Engl. J. Med., 1944, 330: 263–272.)

KNOWN PRIOR ART

Azole compounds in which hydroxy and/or carboxy groups comprise the molecular structure are known to be useful in combatting pathogenic fungi, For example, British Patent No. 2,099,818 and U.S. Pat. No. 4,404,216 disclose Fluconazole

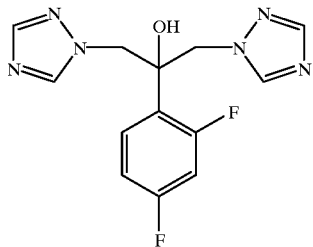

a triazole derivative which has played an important role in protecting against a variety of fungi.

Also, DE-4124942 discloses azoles of the following structure having antithrombotic and fibrinogen-binding activities:

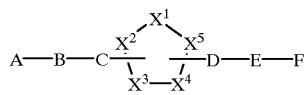

$Q^1 = A-B-C-N<$  $Q^2 = A-B-C-CH<$  $Q^3 = A-B-C-C=$
$Q^4 = F-E-D-N<$  $Q^5 = F-E-D-CH<$  $Q^6 = F-E-D-C=$ wherein: one of $X^1-X^5=Q^1-Q^3$, a second=$Q^4-Q^6$, a third=S, SO, N, $R^1N$, $R^2C$, $(R^2)_2C$, a fourth=O, S, N, $SO_2$, $R^2C$, CO, and a fifth=$R^2C$, $(R^2)_2C$, N; A=cyano, (substituted) phenylene, pyridinylene, pyrazinylene, triazinylene, C=(substituted) phenylene, pyridinylene, pyrimidinylene, pyrazinylene, pyridazinylene, triazinylene, cycloalkylene) cycloalkylene; D=(substituted) alkylene, alkeylene, etc.; E=bond, alkylene, etc., F=carboxy, (substituted) alkoxycarbonyl; $R^1$=H, alkyl, aralkyl, aryl, heteroaryl; R=H, Cl, Br, alkyl, aralkyl, aryl, heteroaryl, alkoxy, $R^1O_2C$, $(R^1)_2N$, etc. These compounds are said to have antithrombotic and fibrinogen-binding activity. The closest example is 4-(4-amidinophenyl)-2-[4-(2-carboxyethyl)phenyl]thiazole.

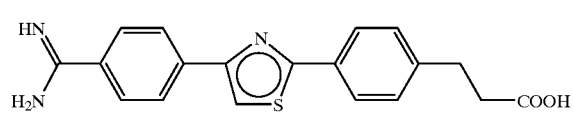

WO-9209586 (FP 0 513387 A1) discloses thiazole derivatives represented by the following structure useful as superoxide radical inhibitors:

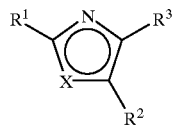

Q

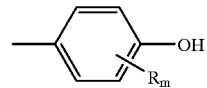

T

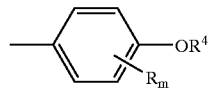

wherein:

$R^1$ is substituted phenyl, pyridyl, thienyl, carbostyril, pyrazyl, pyrrolyl, quinolyl, 3,4-dihydrocarbostyril;

$R^2$ is hydrogen, halo, alkyl, phenyl, alkoxycarbonyl, alkylamino, and the like;

X is sulfur or oxygen;

$R^3$ is Q (supra) wherein R is hydroxyl, carboxylic acid, alkyl, alkenyl and m is 0–2 or, $R^3$ may be T (supra), wherein $R^4$ is hydrogen or alkyl and R is aminoalkyl.

The structure activity relationship (SAR) of the above series has been published in the J. Med. Chem. 1995, 38, 353–358 where the following general structure is shown:

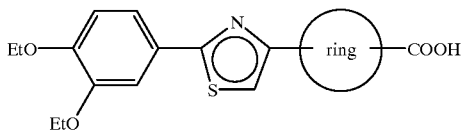

WO-9324472 (EP 0 600092 A1) discloses compounds of the following structure as an active oxygen inhibitor:

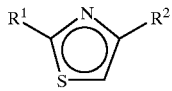

wherein:

$R^1$ is Ph which may be substituted by 1 to 3 alkoxy groups; and $R^2$ is a substituted pyridylcarbonyl which may be substituted by alkoxycarbonyl, carboxyl, a 5 to 15 membered mono-, di-, or tricyclic heterocyclic ring residue having 1 to 3 N, O or S, atoms, or a phenylmoiety of the formula.

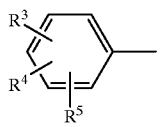

wherein, $R^3$ represents carboxyl, lower alkoxycarbonyl, hydroxyl substituted lower alkyl, lower alkoxy, tri-lower alkyl-substituted silyloxy, hydroxy, or hydrogen; $R^4$ represents hydrogen, lower alkenyl or lower alkyl; $R^5$ represents an amino-lower alkoxycarbonyl which may be substituted further by lower alkyl, amino-lower alkoxy, or lower alkoxy or the like.

U.S. Pat. No. 4,791,200 describes compounds of the following structure useful as antisecretory agents:

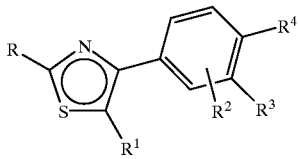

wherein:

R is C1 to C4 alkyl, phenyl, phenyl substituted by $CF_1$, halo selected from I, Br or Cl, C1–C3 alkyl, alkoxy, acetamido, nitro, cyano, alkyamino or dialkylamino having 1–4 carbons or pyridyl;

$R^1$ is H or C1–C4 alkyl, $R^2$ is H, C1–C4 alkyl, C1–C3 alkoxy or, Cl Br or I, $R^3$ or $R^4$ are —O—$(CH_2)_m$—$NR^5R^6$ wherein m=1–3.

Patel and Colah in Bull Haff Instt. (1977), 5, 72–74 disclose p-(2-substituted-4-thiazoly)phenylacetic acid and p-(2-substituted-4-thiazolyl)phenoxyacetic acids useful in treating *tuberculosis* and fungi:

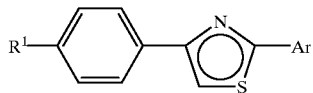

wherein $R^1$ is $CH_2COOH$ or $OCH_2COOH$; and

Ar is phenyl, substituted phenyl or benzyl and the like.

Kirke et al in Bull. Haffkine Inst., (1977), 5, 75–7, and (1974), 2, 28–31 disclose a series of thiazolyl phenoxyacetic acids and derivatives having in vitro antituberculosis and antifungal activity against *T. rubrum* and *T. mentagrophytes,*

Anne et al in Antimicrob. Agents Chemother., (1980), 18(2), 231–9 disclose diaryloxadiazole derivatives having only very weak activity against *Candida albican* ($MIC_{50}$>60 µg/ml) as, for example:

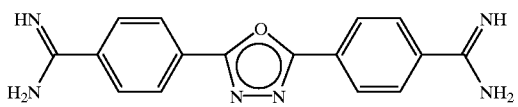

SUMMARY OF THE INVENTION

This invention relates to diaryl substituted azoles and pharmaceutically acceptable salts thereof useful as antifungal agents.

This invention also includes methods for preparing said azoles and antifungal compositions containing these compounds or a pharmaceutically acceptable salt thereof as the active ingredient.

The azoles of this invention are compounds of the general formula:

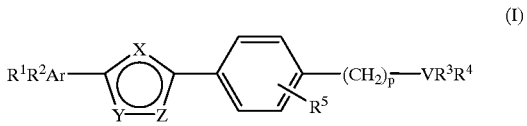

(I)

wherein:

Ar is phenyl, thienyl, pyridyl substituted with $R^1R^2$ where $R^1$, $R^2$ are independently hydrogen or halogen such as F, Cl, Br and I; alkyl, alkenyl, alkynyl, aryl, alkoxy, aryloxy, alkylthio, amino, hydroxyl, cyano, nitro, COCH, aminocarbonyl or aminosulfonyl, alkylamino, diakylamino, acylamino, dialkylaminosulfonyl, alkylaminosulfonyl, alkylamino, dialkylamino, acylamino, dialkylaminosulfonyl, alkylaminosulfonyl or, taken together, $R^1$, $R^2$ may form a ring —O—$(CH_2)_n$—O— wherein n=1,2;

$R^3$, $R^4$ are independently hydrogen, C1–C16 alkyl which may optionally be substituted with amino, dialkylamino, hydroxy, cyano, carboxy; alkenyl, alkynyl, acyl or, taken together, $R^3$ and $R^4$ may be —$(CH_2)m$—Q—$(CH_2)m'$— where m'=m=2, Q=$CH_2$,O, S(O)$_n$, n=0–2, $NR^7$ wherein $R^7$ is C1–C3 alkyl with the proviso that when Q is $CH_2$, m' can also be 1;

$R^5$ is H, halogen as defined above, OR, OH, $NO_2$, $NH_2$ or NHCOR where R is lower alkyl, alkyl or aryl, and the like.

X is N, O or S;

Y is N or S, with the proviso when X=O or S, Y must be N;

Z is N or $CR^8$, where $R^8$ is hydrogen, halogen such as Cl, Br or I, lower alkyl or alkoxycarbonyl, with the proviso that X, Y and Z cannot all be N at the same time.

V is N, O or S, and when V is N, it may also be combined with $R^3$ and $R^4$ to form a heterocycle such as pyrrole, imidazol-1,2,4,-triazole, 1,3,4-triazole and pyrazole, and when V is O or S, $R^3$ and $R^4$ combine to form a single substituent having the definition of $R^4$ alone; and P is an integer having a value of 1–3.

Specifically, this invention relates to thiazoles of the formula:

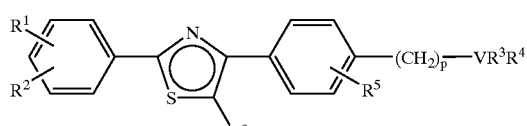
(II)

wherein: $R^1$, $R^2$, $R^3$, $R^4$, $R^5$, p and V are each as defined above in formula (I) and $R^6$ is hydrogen, halogen, carboxy, alkoxy carbonyl, lower alkyl, hydroxy and lower alkoxy and the nontoxic pharmacologically acceptable salts thereof.

This invention also relates to thiadiazoles of the following formula:

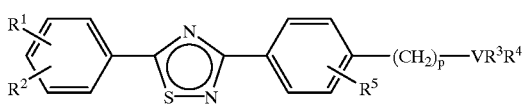
(III)

wherein: $R^1$, $R^2$, $R^3$, $R^4$, $R^5$, p and V are each as defined above in formula (I), and the nontoxic pharmaceutically acceptable salts thereof.

This invention also relates to thiadiazoles of the formula:

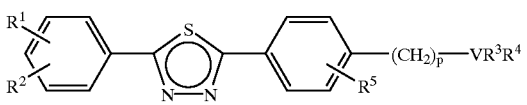
(IV)

wherein: $R^1$, $R^2$, $R^3$, $R^4$, $R^5$, p and V are as defined above in formula (I), and the nontoxic pharmaceutically acceptable salts thereof.

This invention also relates to oxadiazoles of the formula:

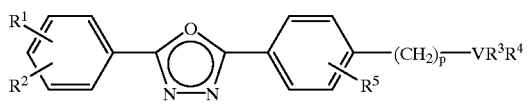
(V)

wherein: $R^1$, $R^2$, $R^3$, $R^4$, $R^5$, p and V are as defined above in formula (I), and the nontoxic pharmaceutically acceptable salts thereof.

More specifically, this invention relates to thiazoles of the formula:

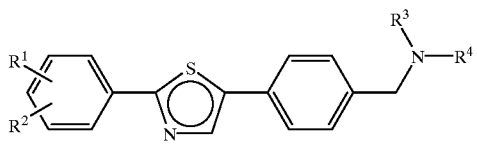
(VI)

wherein: $R^1$, $R^2$, $R^3$, $R^4$, are as defined above in formula (I), and the nontoxic pharmaceutically acceptable salts thereof.

This invention also relate to diazoles of the formula:

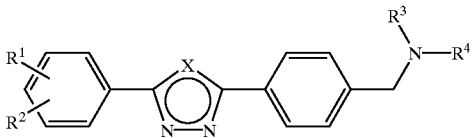
(VII)

wherein: $R^1$, $R^2$, $R^3$, $R^4$ are as defined above and X is O or S, and pharmaceutically acceptable salts thereof.

Alternatively and according to another embodiment, the preferred products of this invention are those represented by the formulae identified as VIII–XIII hereinbelow.

In general, the preferred products are those which conform to formula VIII and formula IX:

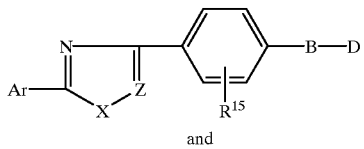
VIII and

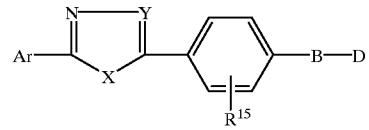
IX wherein:

$A_R$ is selected from among pyridyl, halo substituted pyridyl and

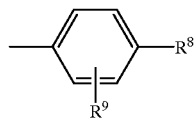

where $R^8$ is hydrogen, halo, nitro, amino, triflouromethoxy, pyrrolyl, lower alkoxy, trifluoromethyl, cyano, lower alkynyl and trimethylsilyl lower alkynyl; and $R^9$ is hydrogen, nitro, lower alkoxy or cyano;

X is S or O;

Y is CH or N;

Z is CH or N;

B is lower alkylene or lower alkynylene;

D is $SR^{10}$, $OR^{11}$ or $N(R^{12}R^{13})$ wherein $R^{10}$ is di-lower alkylaminoalkyl; $R^{11}$ is di-lower alkylaminoalkyl, lower alkenyl, lower alkynyl or lower alkoxyakyl; $R^{12}$ and $R^{13}$ are the same or different and represent hydrogen, lower alkyl, lower alkenyl, lower alkynyl, furfuryl, lower alkoxyalkyl, lower cycloalkyl, lower dialkylaminoalkyl, hydroxy-lower alkyl, lower alkylaminoalkyl, mononuclear lower alkyl, di-lower alkylaminoalkylcarbonyl or, taken together, $R^{12}$ and $R^{13}$ may be combined to form —CH$_2$CH$_2$N(R$^{14}$)CH$_2$CH$_2$— or —CH$_2$CH$_2$SCH$_2$CH$_2$— where $R^{14}$ represents lower alkyl; and $R^{15}$ is hydrogen, nitro, amino, lower alkanamido or hydroxy; and the nontoxic pharmacologically acceptable salts thereof.

Another preferred embodiment are the thiazole compounds represented by formula X:

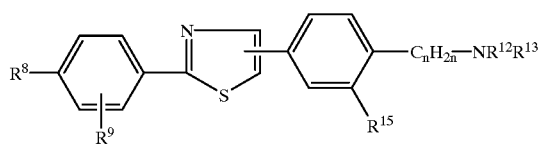

X wherein:
$R^8$ is hydrogen, halo, nitro, amino, triflouromethoxy, pyrrolyl, lower alkoxy, trifluoromethyl, cyano, lower alkynyl, trimethylsilyl lower alkynyl; and $R^9$ is hydrogen, nitro, lower alkoxy or cyano;

$R^{12}$ and $R^{13}$ are the same or different and represent hydrogen, lower alkyl, lower alkenyl, lower alkynyl, furfuryl, lower alkoxyalkyl, lower cycloalkyl, lower dialkylaminoalkyl, hydroxy-lower alkyl, lower alkylaminoalkyl, mononuclear lower alkyl, di-lower alkylaminoalkylcarbonyl or, taken together, $R^{12}$ and $R^{13}$ may be combined to form —CH$_2$CH$_2$N(R$^{14}$)CH$_2$CH$_2$— or —CH$_2$CH$_2$SCH$_2$CH$_2$— wherein $R^{14}$ represents lower alkyl;

$R^{15}$ is hydrogen, nitro, amino, lower alkanamido or hydroxy; and n is an integer having a value of 1 to 3, and the nontoxic pharmacologically acceptable salts thereof.

Still another preferred embodiment are thiazoles of the following formula:

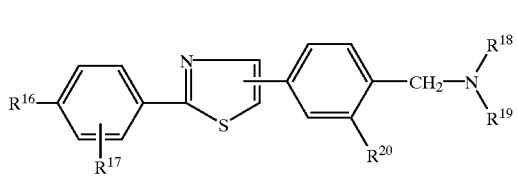

XI wherein:
$R^{16}$ is hydrogen, halo, nitro, lower alkoxy, cyano, trifluoromethyl or lower alkyl;

$R^{17}$ is hydrogen, nitro, halogen or cyano;

$R^{18}$ and $R^{19}$ are the same or different and represent hydrogen, lower alkyl, lower alkenyl, di-lower alkylaminoalkyl, hydroxy lower alkyl and lower alkylaminoalkyl; and $R^{20}$ is hydrogen or hydroxy, and the nontoxic pharmacologically acceptable salts thereof.

Another preferred embodiment provides for diazoles having the formula:

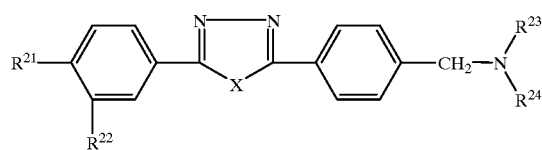

XII wherein:
$R^{21}$ is selected from among hydrogen and lower alkoxy;
$R^{22}$ is selected from among hydrogen and nitro; and
$R^{23}$ and $R^{24}$ are lower alkyl, and the nontoxic pharmacologically acceptable salts thereof.

Also included among the preferred embodiments are thiadiazoles of formula XIII:

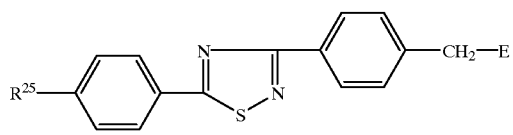

XIII wherein:
E is SR$^{26}$ or NR$^{27}$R$^{28}$ wherein R$^{26}$ is di-lower alkylaminoalkyl R$^{27}$ and R$^{28}$ are the same or different and represent lower alkyl and lower alkenyl, and the nontoxic pharmacologically acceptable salts thereof.

The aforecited compounds are useful in the treatment of broad spectrum fungal infections, and they are also active against a variety of fungi and fungal isolates including Fluconazole-resistant isolates and strains. These compounds are useful for this purpose when used in the concentration range of 250 μg/ml and below.

Appropriate compounds of formula I to XIII are useful in the free base form, in the form of base salts where possible, and in the form of acid addition salts. In practice, use of the salt form is equivalent to use of the base form.

Pharmaceutically acceptable salts within the scope of this invention are those derived from mineral acids such as hydrochloric acid and sulfuric acid and the like including organic acids such as ethanesulfonic acid, benzenesulfonic acid, p-toluenesulfonic acid, and the like. These afford the corresponding hydrochloride, sulfate, ethanesulfonate, benzenesulfonate, p-hydrochloride and the like, respectively; however, this invention is not limited to those mentioned above since equivalent salts will be apparent to those skilled in this art.

Examples of pharmaceutically acceptable base addition salts include organic bases which are nontoxic and of such strength as to form usable salts. These organic bases form a class whose limits are readily understood by those skilled in the art, and for the purposes of illustration, they include mono-, di, and trialkylamines such as methylamine, dimethylamine, and triethylamine; mono-, di-, or trihydroxyalkylamines such as mono-, di-, or triethanolamine, amino acids such as arginine and lysine; guanidine; N-methyl-glucosamine; N-methylglucamine; L-glutamine; N-methylpiperazine; morpholine; ethylenediamine; N-benzylphenethylamine; tris(hydroxymethyl) aminomethane; and the like. (See, for example, "Pharmaceutical Salts," *J. Pharm. Sci.*, 66(1):1–19 (1977).) Salts of inorganic bases include sodium, potassium, calcium or the like.

The acid addition salts of said basic compounds are prepared either by dissolving the free base of compound I to XIII in aqueous or aqueous alcohol solution of other suitable solvents containing appropriate acid and isolating the salt by evaporating the solution, or by reacting the free base of compound I to XIII, having an acid group thereon with a base such that the reactions are in an organic solvent, in which case, the salt separates directly or can be obtained by concentration of the solution. Salts can also be prepared by adding base to an aqueous alcohol solution of another salt.

Generally, the compounds of formulas (I) to (XIII) can be prepared by the processes identified as 1–9 hereinbelow:

Process 1 (Scheme 1):

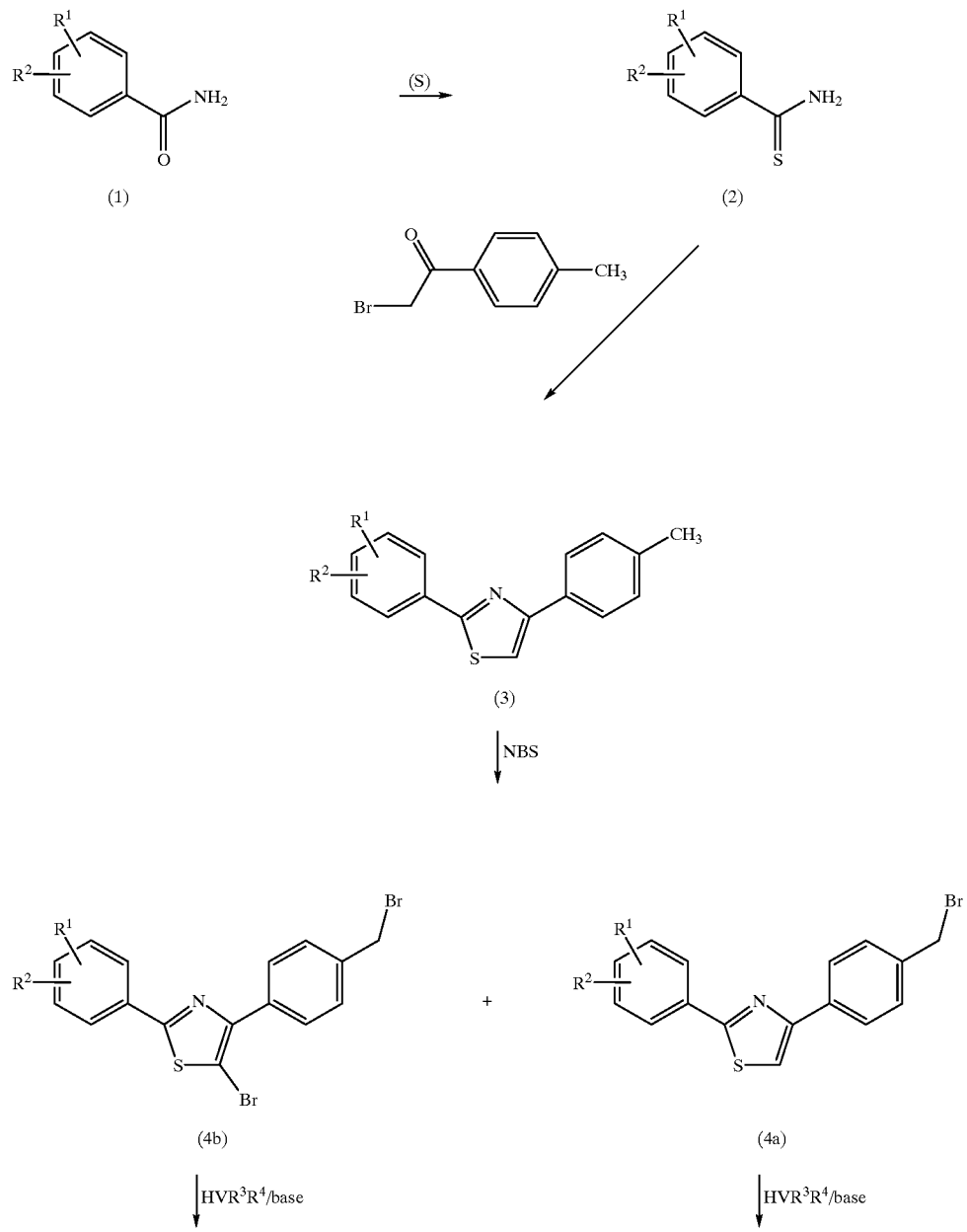

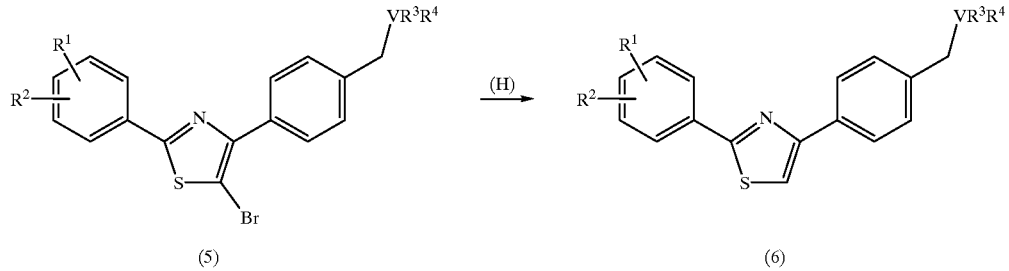

In this process (Scheme 1), the substituted thiobenzamide (2) is prepared according to the literature procedure (Tetrahedron, 41, (22), 5061, 1985, M. Cava and M. Levinson) by refluxing benzamide (1) with Lawesson's reagent in dry benzene or toluene (M. Levinson). A condensation reaction between the thiobenzamide and α-haloacetophenone derivatives in solvent such as low alcohol, THF, $CH_3CN$, etc., gives 2,4-diarylthiazole compounds (3) (Organic Synthesis, Coll. III, 332). The NBS bromination of the compound (3) affords the bromomethyl products (4a) and/or (4b), which are converted to compounds (5) and (6) respectively by reacting with appropriate nucleophile as shown in Scheme 1. Compound (5) can also be de-brominated by catalytic hydrogenation to give compound (6).

Process 2 (Scheme 2):

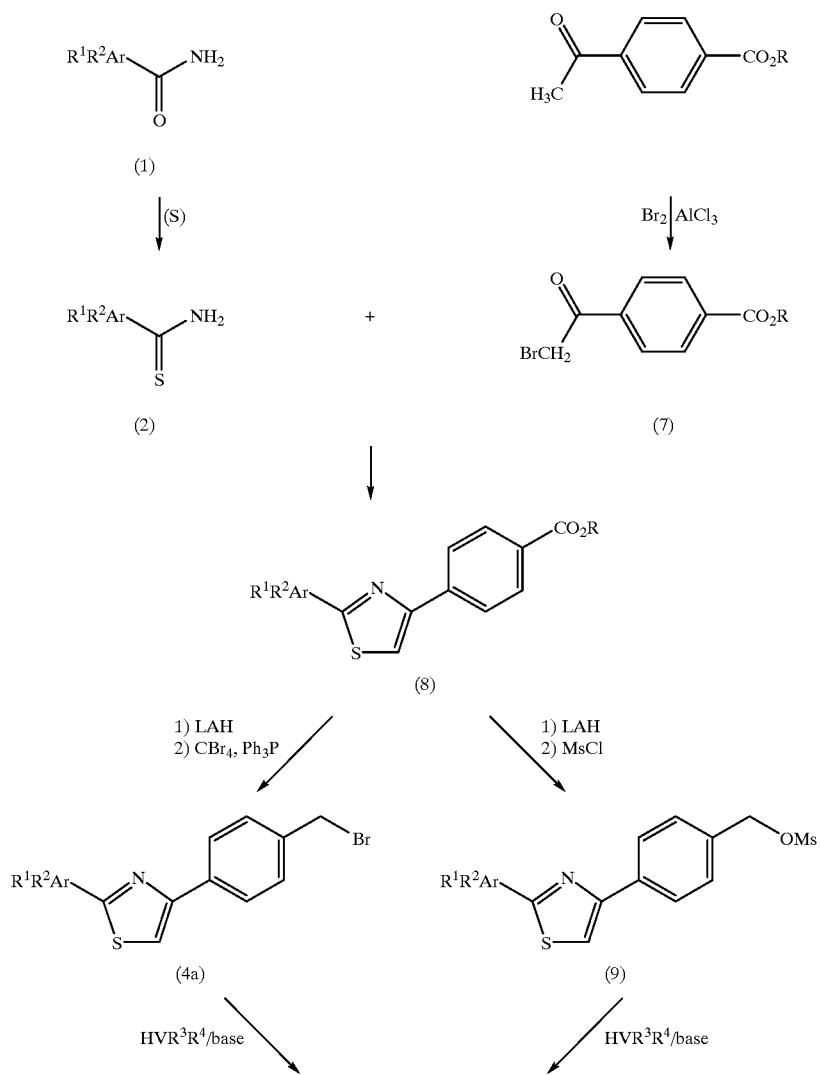

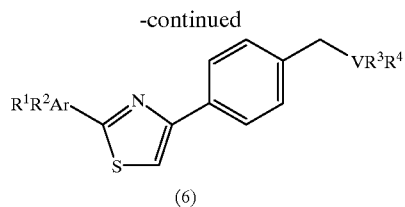

An alternative synthetic pathway is illustrated in Scheme 2, which involves the bromination of ethyl 4-acetylbenzoate with bromine in ether in the presence of catalytic amount of aluminum chloride. The α-bromoacetophenone compound (7) is then condensed with appropriate thiobenzamide (2) as described before to form the diarylthiazole derivatives (8). Subsequent reduction of the ester with LAH followed by bromination with carbontetrabromide and triphenylphosphine yields the bromide (4a) which upon nucleophilic substitution produces the target product (6). Compound (6) can also be prepared through the mesylated intermediate (9), which is prepared by the reduction of compound (8) with LAH followed by mesylation with methanesulfonyl chloride.

A compound represented by the general formula (II) wherein p=2–3 can be prepared by the process as shown in Scheme 3 and Scheme 4:

Process 3 (Scheme 3):

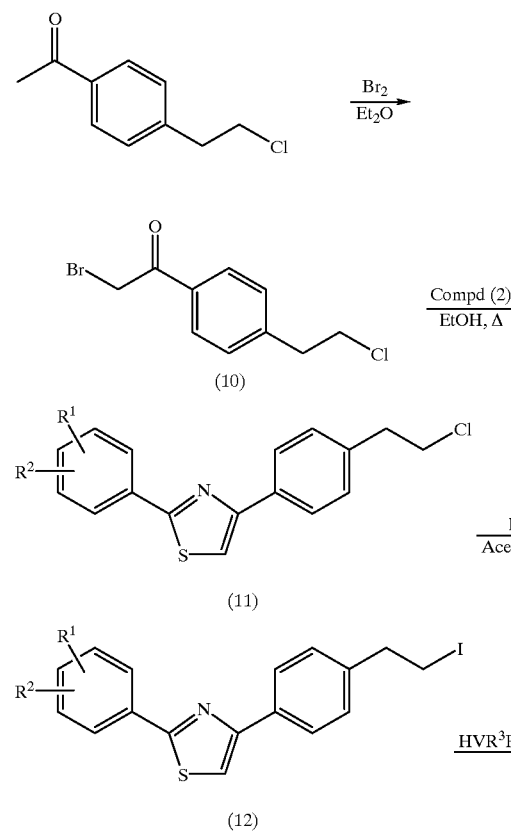

Compound (11) is obtained by condensation and cyclization thiobenzamide (2) and α-bromoaceophenone (10) which is made by the bromination reaction as described before. By refluxing compound (11) in acetone with excess amount of NaI produces the iodoanalog (12) which on reaction with nucleophile produces product (13).

Process 4 (Scheme 4)

In order to prepare a compound represented by the general formula (11) wherein p=3, a palladium-catalyzed C—C coupling reaction between the 4-(p-bromophenyl)thiazole derivatives (14) and an acetylenic reactant is employed. Catalytic hydrogenation of the coupling product (15) gives the extended three carbon side chain compounds (16) in very good yield (Scheme 4).

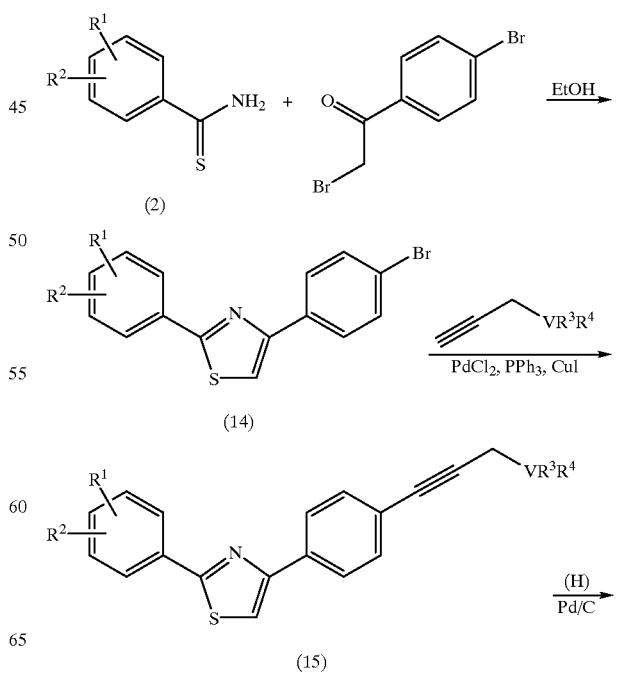

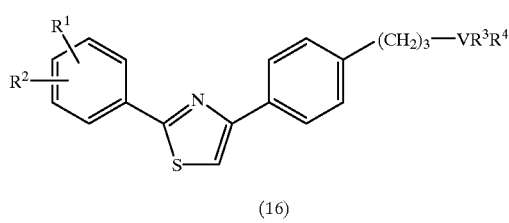

(16)

Process 5 (Scheme 5)

Scheme 5

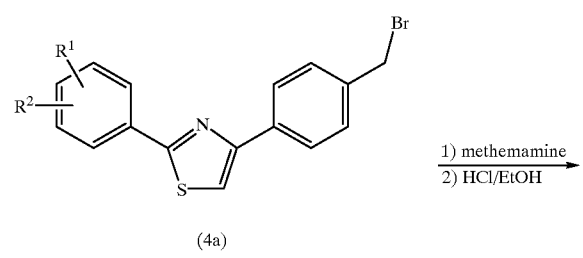

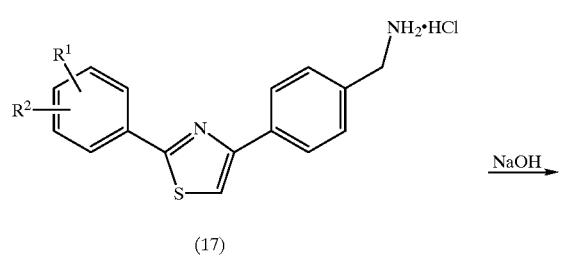

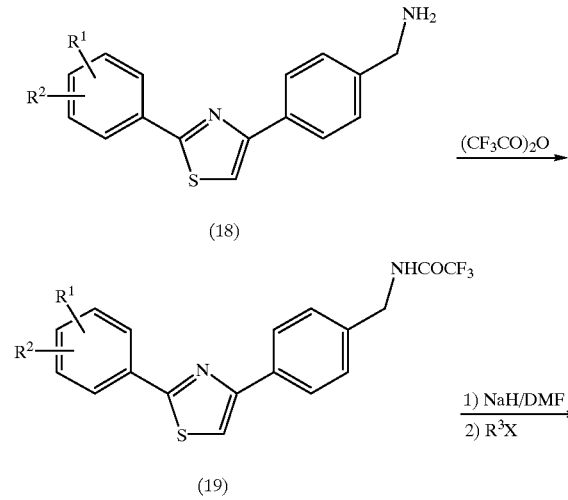

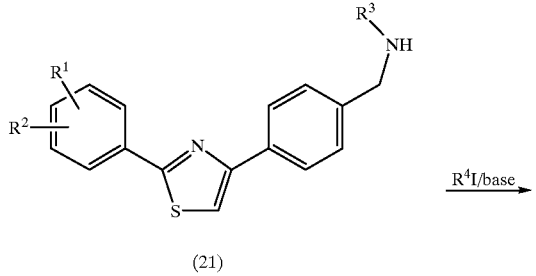

Primary amine sidechain compounds (18) can be prepared from the bromo compounds (4a) by the use of methenamine followed by cleavage of the resulting quaternary amine salts with ethanolic HCl (Organic Synthesis, Coll. V, 212). The secondary amine sidechain compounds (21) (Scheme 5) are prepared by acetylation of compounds (18) with trifluoroacetic anhydride to give the amide analogs (19) quantitatively. Treatment of the compound (19) with NaH in anhydrous DMF followed by alkylation with alkyl halide affords compound (20), which can be converted to the secondary amine products (21) by cleavage of the trifluoroacetyl group in a basic media. Compound (21) is transformed to target compounds (6) by treatment with base such as $K_2CO_3$ and appropriate alkyl halide.

Process 6 (Scheme 6)

Scheme 6

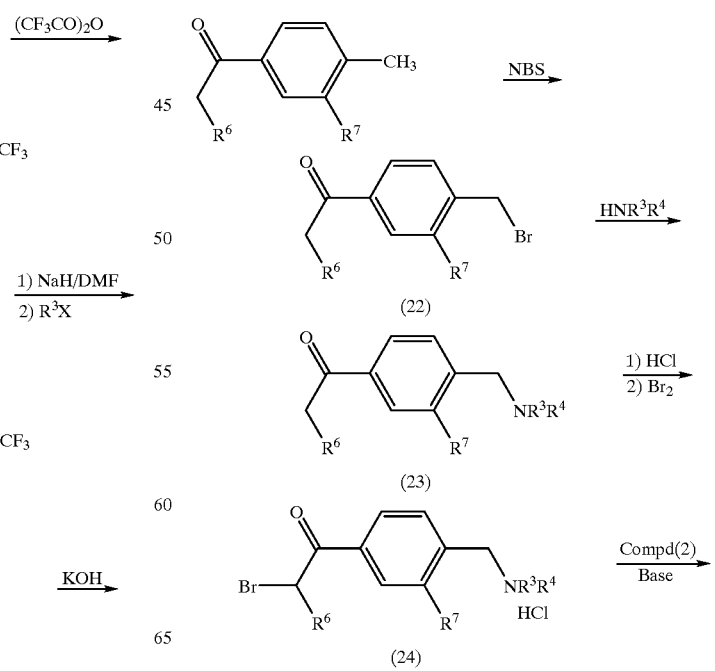

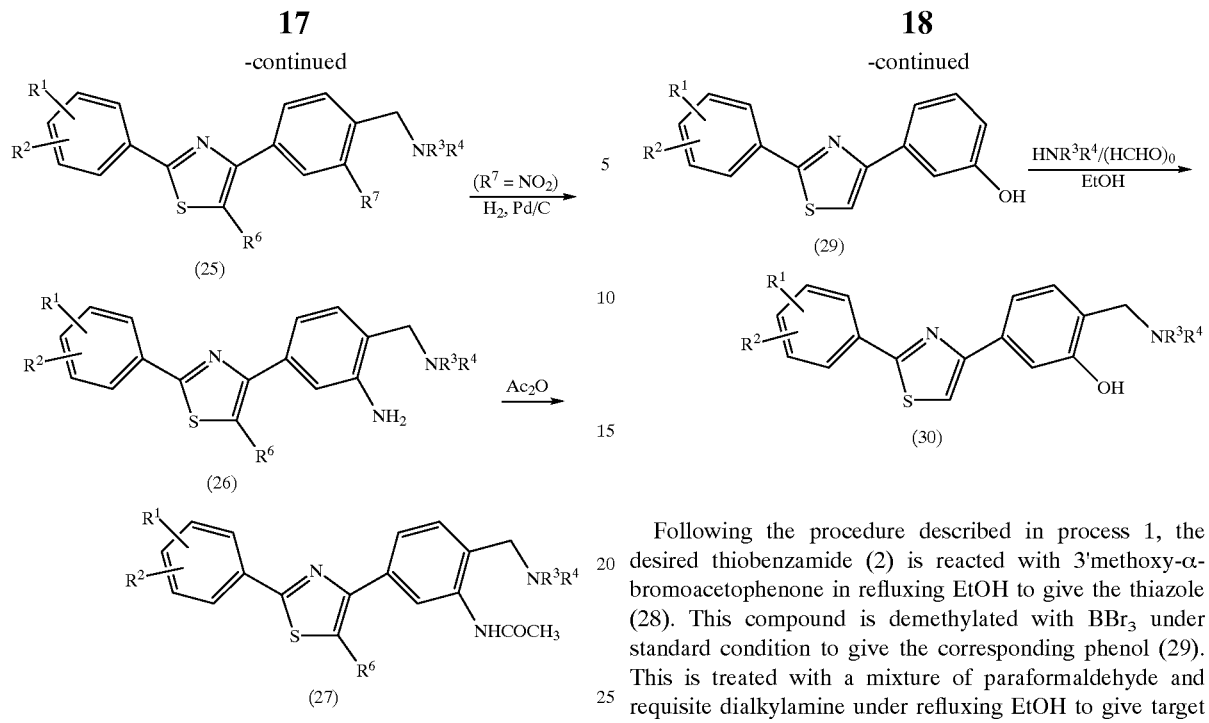

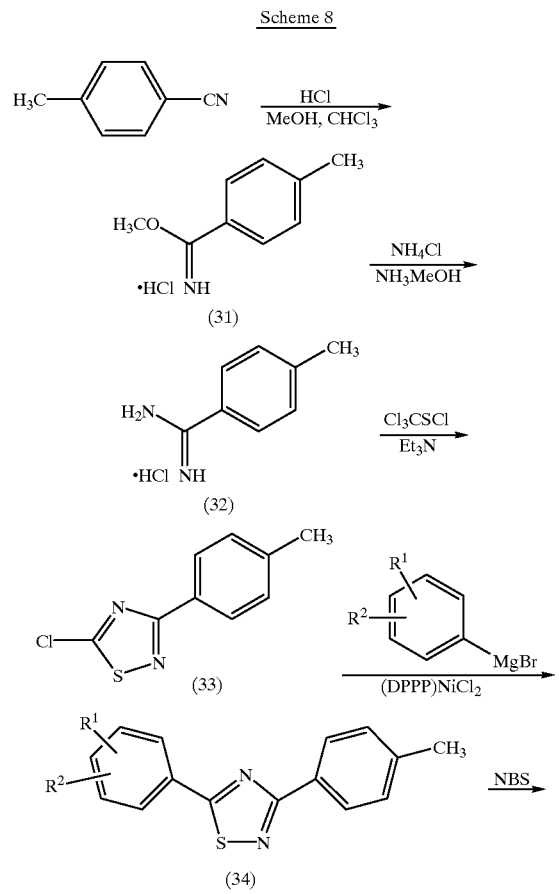

The α-bromoacetophenones with the desired dialkylamino alkyl groups (23) are synthesized and coupled with substituted thiobenzamides (2) to give target compounds (Scheme 6). 4'-Methyl acetophenone or derivatives thereof are treated with NBS in $CCl_4$ under refluxing condition to give the corresponding benzylbromides (22) which are subsequently treated with the requisite dialkylamines at room temperature to give the dialkylamino alkyl derivatives (23). These compounds are purified via flash chromatography, converted to the corresponding HCl salt, and brominated with $Br_2$ to give α-bromoacetophenones (24). Compounds (24) are reacted with substituted thiobenzamides (2) under refluxing EtOH or similar solvent to give the target compounds (25) as a mixture of HCl and HBr salts. These are converted to the free base and purified via flash chromatography as needed. Compounds wherein $R^7$ is not hydrogen are further derivatized to additional targets. For example, compound (25) ($R^7=NH_2$) which is eventually treated with $Ac_2O$ to give the N-acetylamino compound (27) ($R^7$= $NHCOCH_3$).

Process 7 (Scheme 7)

Scheme 7

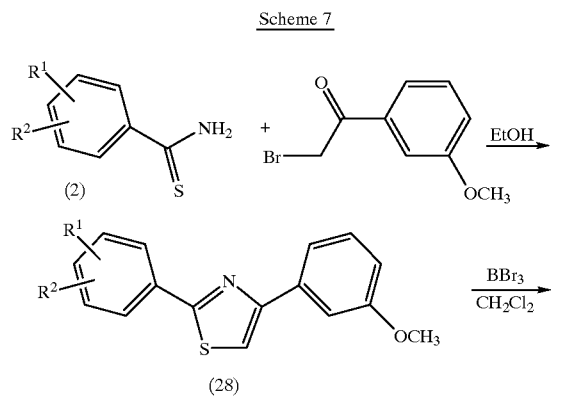

Following the procedure described in process 1, the desired thiobenzamide (2) is reacted with 3'methoxy-α-bromoacetophenone in refluxing EtOH to give the thiazole (28). This compound is demethylated with $BBr_3$ under standard condition to give the corresponding phenol (29). This is treated with a mixture of paraformaldehyde and requisite dialkylamine under refluxing EtOH to give target dialkylaminomethyl compounds (30).

Process 8 (Scheme 8)

A compound represented by the general formula (III) can be prepared by the process as shown in Scheme 8:

-continued

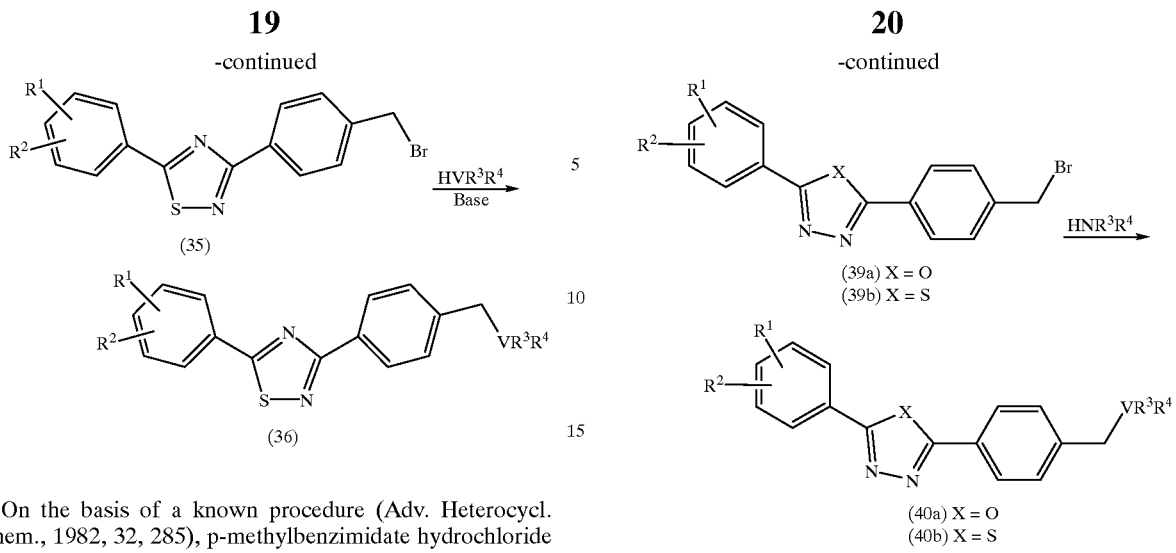

On the basis of a known procedure (Adv. Heterocycl. Chem., 1982, 32, 285), p-methylbenzimidate hydrochloride (31) is prepared by bubbling hydrogen chloride gas through a cooled solution of p-tolunitrile in mixed solvents (1:1= chloroform and methanol). Treatment of benzimidate (31) with ammonia/methanol solution gives amidine hydrochloride (32) with ammonia/methanol solution gives amidine hydrochloride (32) quantitatively. The amidine (32) is then reacted with one equivalent of perchloromethylmercaptan in the presence of triethylamine at zero degree to give a cyclized product, 5-chloro-1,2,4-thiadiazole (33) as yellow solid. Coupling of 5-chloro-1,2,4-thiadiazole with substituted aryl Grigriard Reagents in dry THF provides the desired diaryl 1,2,4-thiadiazoles (34) (J. Am. Chem. Soc., 1985, 107, 2033 and organometallics, 1993, 12, 3468). Subsequent bromination followed by nucleophilic substitution as described in Preparation Process 1, affords the final product (36).

Process 9 (Scheme 9)

A compound represented by the general formula (IV) and (V) can be prepared by the following process:

Scheme 9

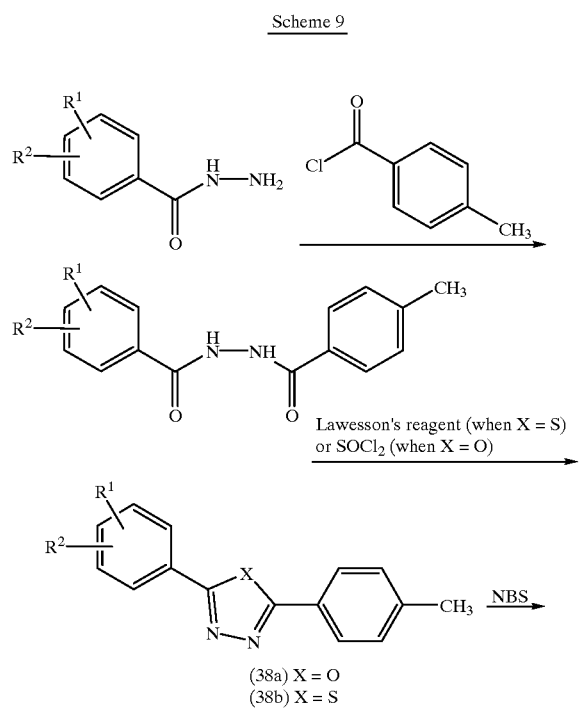

The N,N'-diacylhydrazine compound (J. Chem.Soc. (C), 1970, 1397) (37) is prepared by acylation of the substituted benzhydrazide at zero degree with p-methylbenzoyl chloride. The N,N'-diacylhydrazine compound (37) is heated either with thionyl chloride to produce the cyclized product, 1,3,4-oxadiazole (38a) or with Lawesson's Reagent* to exchange the oxygen to give sulfur and then cyclize to 1,3,4-thiadiazoles (38b). The cyclized products (38a & 38b) are treated with N-bromosuccinimide to give bromomethyl compounds (39a & 39b) which are reacted with appropriate nucleophiles to afford desired products (40a) and (40b) respectively.

*Lawesson's Reagent is (2,4-bis(4-methoxyphenyl)-1,3-dithia-2,4-disulfide and the use of the reagent in various processes is described by M. D. Cara and M. I. Levinson in Tetrahedron; Vol. 41: pages 5061 et seq. (1985).

One of ordinary skill in the art will recognize variations in the sequence and variations in the appropriate reaction conditions from the analogous reactions shown or otherwise known which may be appropriately used in the processes above to make the compounds of Formulae I to XIII herein.

EXAMPLE 1

2-(4'-fluorophenyl)-4-[4"-(N-methyl-N-allylaminomethyl) phenyl]thiazole(VI: $R_1$=H, $R_2$=4.F, $R_3$=Me, $R_4$=allyl, V=N (Process 1, Scheme 1)

4-Fluorobenzamide (5.0 g, 35.9 mmol) in benzene (100 ml) is added Lawesson's reagent (7.27 g, 18.0 mmol) and the resulting solution is heated to reflux for 1 hour. The solution is cooled to room temperature, concentrated and water (150 ml) added. The mixture is heated to reflux for 3 hours, and cooled to room temperature. The precipitate is filtered and dried under vacuum to yield 4-fluorothiobenzamide as a yellow solid (4.1 g, 71%).

$^1$H NMR (CDCl$_3$): δ 7.09 (t, 2H), 7.90(dd, 2H).

To a solution of the crude product of 4-fluorothiobenzamide (2.0 g, 12.9 mmol) in EtOH (30 ml) is added 2-bromo-4' methylacetophenone (2.75 g, 12.9 mmol). The mixture is heated to reflux for 24 hours. The course of the reaction is followed by thin layer chromatography. Upon completion of the reaction the solution is cooled to room temperature and the white precipitate filtered and dried under vacuum to yield 2-(4'-fluorophenyl)-4-(p-tolyl) thiazole (1.54 g, 54%).

$^1$H NMR (DMSO$_{d6}$): δ 2.35 (s, 1H), 7.28 (d, 2H), 7.38 (t, 2H), 7.94 (d, 2H), 8.08 (dd, 2H), 8.11 (s, 1H).

To a solution of 2-(4'-fluorophenyl)-4-(p-tolyl)-thiazole (1.49 g, 5.5 mmol) in CC$_4$ (50 ml) is added NBS (1.09 g, 6.1 mmol) and benzoyl peroxide (50 mg) and the reaction mixture is heated to reflux. An additional 50 mg of benzoyl peroxide is added every hour for 4 hours. The mixture is refluxed for 24 hours and then filtered through celite. The mother liquor is concentrated to yield a yellow oil which is triturated with pentane and filtered to yield 2-(4'-fluorophenyl)-4-[p-(bromomethyl)phenyl)]thiazole (1.45 g, 75%).

$^1$H NMR (DMSO$_{d6}$): δ 4.77 (s, 2H), 7.39 (t, 2H), 7.58 (d, 2H), 8.08 (m, 2H), 8.22 (s, 1H).

To a solution of 2-(4'-fluorophenyl)-4-(p-bromomethylphenyl)-thiazole (1.00 g, 2.87 mmol) in EtOH (20 ml) is added dropwise N-methyl allylamine (0.45 g, 6.00 mmol) in EtOH (10 ml). The solution is stirred at room temperature for 12 hours and the solvent is removed under reduced pressure to yield a green oil. The oil is taken up in CH$_2$Cl$_2$ (30 ml) and washed with 1N NaCH (30 ml) and brine (30 ml). The organic layer is dried over anhydrous K$_2$CO$_3$ and concentrated. The residue is chromatographed on a silica gel column eluting with MeOH:CHCl$_3$ (5:95) to yield a yellow oil. The resulting oil is dissolved in MeOH (5 ml) to which is added excess HCl/MeOH solution (10% w/w, 1 ml) and stirred for 1 hour. The solvent is removed under reduced pressure, and the residue recrystallized from isopropanol to yield the title compound as HCl salt as a brown solid (0.43 g, 40%).

$^1$H NMR (DMSO$_{d6}$) δ 2.60 (d, 3H), 3.70 (m, 2H), 4.35 (m, 2H), 5.51 (s, 1H), 5.59 (d, 1H), 6.08 (m, 1H), 7.40 (t, 2H), 7.72 (d, 2H), 8.12 (m, 4H), 8.30 (s, 1H)

EXAMPLE 1a 2-(4'-Chlorophenyl)-4-[[4'-(2-N,N-dimethylaminoethyl)thio]methyl]phenyl]thiazole(II: R$^1$=H, R$^2$=4.Cl, V=S, R$^3$, R$^4$=CH$_2$CH$_2$NMe$_2$, R$^6$=H)

Replacing 4-fluorobenzamide with 4-chlorobenzamide in the above experiment the compound 2-(4'-chlorophenyl)-4-[(p-bromomethyl)phenyl]thiazole is obtained. 2-Dimethylaminoethanethiol hydrochloride (0.7 g, 5.0 mmol) is added to a slurry of NaH (60%, 0.44 g, 11 mmol) in THF (20 ml) and the suspension stirred for 1 h. A solution of the above bromomethyl compound (1.82 g, 5.0 mmol) in THF (20 ml) is added with stirring and the reaction mixture stirred for 4 h. THF is distilled, the residue is poured into water and the mixture is extracted with EtOAc. The EtOAc extract is washed with brine, dried, stripped and the residue chromatographed (SiO$_2$, 100 g, CHCl$_3$-CHCl$_3$/MeOH 5%) to give the title compound as a soft solid (0.75 g), mp. 51–52° C.

$^1$H NMR (CDCl$_3$): 2.20 (s, 6 H), 2.40–2.60 (m, 4 H), 3.80 (s, 2 H), 7.35–7.50 (m, 5 H), 7.85–8.00 (m, 4 H).

EXAMPLE 1b 2-(4'-Chlorophenyl-4-[[4-(N-methylpiperazinyl)methyl]phenyl]thiazole (II: R$^1$=H, R$^2$=4.Cl, V=N, R$^3$R$^4$=(CH$_2$CH$_2$)$_2$NMe, R$^6$=H)

To a suspension of 2-(4'chlorophenyl)-4-[(p-bromomethyl)phenyl]-thiazole (1.0 g, 2.74 mmol) and anhydrous K$_2$CO$_3$ (0.83 g, 6 mmol) in DMF (15 ml) is added a solution of N-methyl piperazine (0.3 ml, 2.74 mmol) in DMF (1 ml) with stirring. The reaction mixture is stirred for 18 h at rt. It is poured into water (100 ml) and the organic material is extracted with EtOAc. The EtOAc layer is washed with brine, dried, stripped, and the residue chromatographed (SiO$_2$, 30 g, CHCl$_3$/CHCl$_3$/MeOH 5%) to give the title compound (0.43 g), mp. 110–111° C.

$^1$H NMR (CDCl$_3$): 2.25 (s, 6 H), 2.35–2.60 (br s, 8 H), 3.55 (s, 2 H), 7.35–7.50 (m, 5 H), 7.90–8.05 (m, 4 H).

Additional examples are shown in Table I.

EXAMPLE 2

2-(4'-methoxyphenyl)-4-[4"-(N-allyl-N-methylaminomethyl)phenyl]thiazole(VI: R$_1$=H, R$_2$=4-MeO, R$_3$=Me, R$_4$=allyl)

(Process 2, Scheme 2)

To a solution of ethyl 4-acetylbenzoate (5.12 g, 26.6 mmol) in ether (50 ml) containing aluminium chloride (0.025 g, 0.19 mmol) is added bromine (1.31 ml, 26.6 mmol) and the reaction mixture is stirred for 2 h. The reaction mixture is poured into saturated NaHCO$_3$ solution and stirred for 30 min. and the layers are separated. The organic layer is washed with NaHCO$_3$, H$_2$O, dried over MgSO$_4$, concentrated to half of its volume and refrigerated overnight. The resulting solid is filtered to yield ethyl 4-(2'-bromoacetyl) benzoate (5.89 g, 81.6%) as white crystals.

$^1$H NMR (CDCl$_3$): δ 1.42 (t, 3H), 4.42 (q, 2H), 4.48 (s, 3H), 8.04 (d, 2H), 8.16 (d, 2H).

To a solution of 4-methoxythiobenzamide (1.50 g, 8.97 mmol) in ethanol (50 ml) is added ethyl 4-(2'-bromoacetyl) benzoate (2.43 g, 8.97 mmol) and the reaction mixture is heated to reflux for 4 hours. The reaction mixture is cooled to room temperature and the precipitate is filtered to yield ethyl p-[2-(4'-methoxy)phenyl-thiazol-4-yl]benzoate (2.15 g, 70.1%) as a light yellow solid.

$^1$H NMR (CDCl$_3$): δ 1.42 (t, 3H), 3.87 (s, 3H), 4.40 (q, 3H), 6.98 (d, 2H), 7.53 (s, 1H), 7.96–8.14 (m, 6H).

To a slurry of LAH (167 mg, 4.41 mmol) in dry THF (10 ml) is added dropwise a solution of ethyl p-[2-(4'-methoxyphenyl)-thiazol-4-yl]benzoate (500 mg, 1.47 mmol) in dry THF (10 ml) and the reaction mixture is stirred at room temperature for 18 hours. A solution of saturated (NH$_4$)$_2$SO$_4$ (20 ml) is added to the reaction mixture and stirred for 30 min. The precipitate is filtered, and the aqueous layer is washed thoroughly with ethyl acetate. The combined organic layer is washed with H$_2$O and brine, dried over MgSO$_4$ and concentrated in vacuo to yield 2-(4'-methoxyphenyl)-4-(4"-hydroxymethylphenyl)-thiazole (360 mg, 82.2%) as a white solid.

$^1$H NMR (CDCl$_3$): δ 3.89 (s, 3H), 4.76 (s, 2H), 6.98 (d, 2H), 7.42 (s, 1H), 7.46 (d, 2), 7.97–8.02 (m, 4H).

To a solution of 2-(4'-methoxyphenyl)-4-(4"-hydroxymethylphenyl)-thiazole (355 mg, 1.13 mmol) in dry THF (10 ml) at 0° C. is added triphenylphosphine (446 mg, 1.70 mmol) and carbon tetrabromide (564 mg, 1.70 mmol). The reaction mixture is stirred for 17.5 h at 0° C. The precipitate is filtered and the filtercake is washed with THF. The filtrate is concentrated in vacuum and purified by column chromatography eluting with 10% ethyl acetate/hexane to yield 2-(4'-methoxyphenyl)-4-(4"-bromomethylphenyl)-thiazole (285 mg, 70%) as a white solid.

$^1$H NMR (CDCl$_3$): δ 3.88 (s, 3H), 4.56 (s, 2H), 6.98 (d, 2H), 7.43 (s, 1H), 7.46 (d, 2H) 7.95–8.01 (m, 4H).

The above bromomethyl compound is aminated following the procedure as described in Example 1 giving the title compound 2-(4'-methoxyphenyl)-4-[4"-(N-allyl-N-methylaminomethyl)phenyl]-thiazole in 95% yield.

$^1$H NMR (CDCl$_3$): δ 2.51 (s,3H), 3.56–3.90 (m, 2H), 3.85 (s, 3H), 4.19–4.46 (m, 2H), 5.51–5.60 (m, 2H), 5.98–6.29 (m, 1H), 7.11 (d, 2H), 7.70 (d, 2H), 7.98 (d, 2H), 8.12 (d, 2H), 8.20 (s, 1H), 11.12 (br s, 1H).

EXAMPLE 2a (Process 2, Scheme 2)

2-(4-Pyridyl)-4-[[4"-(N-methyl-N-propylamino)methyl]phenyl]thiazole (I, R$_1$R$^2$—Ar=4-py, R$_3$=propyl, R$_4$=Me, R$^5$=H, p=1, V=N)

2-(4-Pyridyl)-4-[(4"-hydroxymethyl)phenyl]thiazole is prepared by following the above procedure in Example 2.

A solution of methanesulfonylchloride (0.75 mL, 9.11 mmol) in THF (5 mL) is added with stirring to an ice-cold solution of the above alcohol (0.83 g, 3.09 mmol) in THF (70 mL) containing Et$_3$N (0.92 mL, 9.11 mmol). After the addition is over the reaction mixture is allowed to warm up to room temperature and eventually refluxed for 2 h to complete the reaction. The reaction mixture is cooled and filtered. The residue is washed with CHCl$_3$ and dried to give the desired compound as a yellow solid (0.45 g).

$^1$H NMR (DMSO$_{d6}$): δ 2.35 (s, 3 H), 4.84 (s, 2 H), 7.59 (d, 2 H), 8.13 (d, 2 H), 8.43(d, 2 H), 8.95 (d, 2 H).

A solution of the above mesylate (0.45 g, 1.3 mmol) and N-methyl-N-propyl amine (0.33 mL, 3.25 mmol) in THF (50 mL) is heated at 55° C. for 18 h. The reaction mixture is stripped and flash chromatographed (SiO$_2$, CHCl$_3$/MeOH 5%) to give 0.238 g of title compound.

$^1$H NMR (CHCl$_3$): δ 0.86 (t, 3 H), 1.38–1.60 (m, 2 H), 2.13 (s, 3 H), 2.30 (t, 2 H), 3.49 (s, 2 H), 7.40 (d, 2 H), 7.95–8.04 (dd, 4 H), 8.32 (s, 1 H), 8.75 (d, 2 H).

It was converted to dihydrochloride salt, mp. 192–195° C. Additional examples are shown in Table I.

EXAMPLE 3

(Process 3, Scheme 3)

2-(4'-methoxyphenyl)-4-[4Ó-[2-(N,N-dimethylamino)-ethyl]phenyl]thiazole (II: R$^1$=H, R$^2$=4CH$_3$O, R$^3$=R$^4$=CH$_3$, R$^5$=H, R$^6$=H, V=N, p=2)

To a solution of 4'-(2-chloroethyl)acetophenone (5.00 g, 27.37 mmol) and aluminum chloride (0.30 g, 2.73 mmol) in anhydrous diethyl ether(75 ml) is added bromine (4.37 g, 27.37 mmol) dropwise. After 18 hours the solution is concentrated and the residue is taken up in CHCl$_3$ (75 ml) and washed with water (75 ml). The organic layer is dried over MgSO$_4$ and concentrated to yield 7.91 g crude bromo product as a dark oil which is used as is without further purification.

A mixture of α-bromo-4'-(2-chloroethyl)acetophenone, (1.56 g, 5.98 mmol) and 4-methoxythiobenzamide (1.00 g, 5.98 mmol) is heated to reflux in EtOH (25 ml) for 2 hours. The mixture is then cooled to 5° C. and the precipitate filtered and dried to yield 2-(4Ó-methoxyphenyl)-4-[4Ó-(2-chloroethyl)phenyl]thiazole (0.90 g, 46%).

A solution of 2-(4'-methoxyphenyl)-4-[4Ó-(2-chloroethyl)phenyl]-thiazole (0.30 g, 0.71 mmol) and excess (2 ml) dimethyl amine/EtOH solution (19% w/w) in THF (10 ml) is placed into a sealed reaction vessel and heated to 80° C. for 20 hours. The solution is then concentrated and the residue taken up in CHCl$_3$(20 ml) and washed with saturated NaHCO$_3$ (20 ml). The organic layer is dried over MgSO$_4$ and concentrated to yield an oil which is purified on a silica gel column eluting with 10% MeOH/CHCl$_3$ to yield the title compound as an off white solid (90 mg, 37%).

$^1$H NMR (CDCl$_3$): δ 2.33 (s, 6H), 2.60 (m, 2H), 2.80 (m, 2H), 3.86 (s,3H), 6.97 (d, 2H), 7.27 (d, 2H), 7.35 (s, 1H), 7.89 (d, 2H), 7.97 (d, 2H).

Additional examples are shown in Table I.

EXAMPLE 4

(Process 4, Scheme 4)

2-(4'-Fluorophenyl)-4-[4'-[3-(N,N-dimethylamino)-propyl]phenyl]thiazole (II: R$^1$=H, R$^2$=4.F, p=3, V=N, R$^3$=R$^4$=CH$_3$)

To a solution of p-fluorothiobenzamide (0.39 g, 2.5 mmol) in 20 mL of abs. EtOH is added 2,4'-dibromoacetophenone (0.7 g, 2.5 mmol) all at once. The reaction mixture is stirred at room temperature for 3 hours and then chilled in ice bath. The precipitate is collected by filtration, washed with cold EtOH (5 ml×2) and dried in vacuum to give 2-(4'-fluorophenyl)-4-(4'-bromophenyl)thiazole as a white fluffy crystaline solid (1.55 g, 93%). mp.158–9° C.

$^1$H NMR (CDCl$_3$): δ 7.16 (t, 2H), 7.47 (s, 1H), 7.58 (d, 2H), 7.87 (d, 2H), 8.02 (m, 2H).

In a 100 ml flask is placed triphenylphosphine (80 mg, 10%), PdCl$_2$ (40 mg, 5%) and 2-(4'-fluorophenyl)-4-(4'-bromophenyl)thiazole (0.98 g, 2.9 mmol) in 20 mL of diethylamine. After stirring for 15 min under N$_2$ atmosphere, CuI (30 mg, 5%) and 1-dimethylamino-2-propyne (0.27 g, 3.18 mmol) in 20 ml of acetonitrile are added to the mixture. After 18 h of heating, the solvent is evaporated under reduced pressure and the residue is filtered through silica gel pad (50 g) using CHCl$_3$ (400 mL) and 2% MeOH in CHCl$_3$(400 mL). A large portion of unreacted 2-(4'-fluorophenyl)-4-(4'-bromophenyl)thiazole is recovered after removal of chloroform filtrate (0.55 g, 56%). The second part of the filtrate (29 MeOH in CHCl$_3$) is concentrated and the residual solid is then purified over silca gel column eluting with 2% MeOH in CHCl$_3$, 2-(4'-fluorophenyl)-4-[4'-(3-dimethylamino-2-propyn-1-yl)phenyl]thiazole is obtained after concentration and trituration with hexane (0.25 g, 27% yield), mp. 98–9° C.

$^1$H NMR (CDCl$_3$): δ 2.39 (s, 6H), 3.50 (s, 2H), 7.16 (t, 2H), 7.48 (s, 1H), 7.51 (d, 2H), 7.93 (d, 2H), 8.03 (m, 2H).

A warm solution of 2-(4'-fluorophenyl)-4-[4'-(1-dimethylamino-2-propyn-3-yl)phenyl]thiazole (0.2 g, 0.6 mmol) in abs. EtOH (20 mL) containing a catalytic amount of palladium on activated carbon (5%, 20 mg) is shaked under hydrogen atomsphere (30 psi) for 2 h. After removal of the catalyst by filtration, the filtrate is concentrated to give 2-(4'-fluorophenyl)-4-[4'-(3-N,N-dimethylaminopropyl) phenyl]thiazole as desired product (0.18 g, 89%).

$^1$H NMR (CDCl$_3$): δ 1.65 (m, 2H), 2.24 (s, 6H), 2.32 (t, 2H), 2.69 (t, 2H), 7.14 (t, 2H), 7.27 (d, 2H) 7.40 (s, 1H), 7.89 (d, 2H), 8.02 (m, 2H).

Additional examples are shown in Table I.

EXAMPLE 5

(Process 5, Scheme 5)

2-(4'-Chlorophenyl-4-[[4'-(N-pentyl)aminomethyl]phenyl]thiazole (VI; R$_1$=H, R$_2$=4.Cl, R$_3$=n-pentyl, R$^4$=H)

To a boiling solution of methenamine (1.1 g, 7.85 mmol) in CCl$_4$ (80 mL) is added dropwise a solution of 2-(4'-chlorophenyl)-4-[4'-bromomethyl)phenyl]thiazole (Scheme 1; 2.6 g, 7.13 mmol) in CHCl$_3$ (40 mL). The reaction mixture is refluxed for 3 h under N$_2$ and cooled. The white precipitate is filtered and the residue washed with a small volume of CHCl$_3$ and air dried to give the quaternary salt (2.7 g). Conc. HCl (4 mL) is added dropwise with stirring to a suspension of the above salt (2.7 g) in EtOH (30 mL) and the reaction mixture is heated to reflux for 3 h. It is cooled, filtered and the residue is washed with a small volume of EtOH and dried to give the desired amine hydrochloride (1.97 g). mp. >320° C. $^1$H NMR (DMSO-d$_6$): δ 4.05 (s, 2 H), 7.43–7.63 (m, 4 H), 7.95–8.13 (m, 5 H).

To an aqueous suspension of the above salt is added an aqueous solution of NaOH (6 N) to pH 12, and the free base is extracted with CH$_2$Cl$_2$. The extract is dried and evaporated to give the corresponding amine, 2-(4'-chlorophenyl)-4-[4'-(aminomethyl) phenyl]thiazole (1.4 g).

$^1$H NMR (DMSO-d$_6$): δ 3.75 (s, 2 H), 7.43 (d, 2 H), 7.60 (d, 2 H), 7.98 (d, 2 H), 8.06 (d, 2 H), 8.16 (s, 1 H).

A solution of trifluoroacetic anhydride (0.85 mL, 6 mmol) in THF (5 mL) is added dropwise to a solution of the above amine (1.4 g, 4.7 mmol) in THF (15 mL) and the reaction mixture stirred for 18 h at room temperature. The THF is evaporated and the residue triturated with a small volume of ether. The solid is filtered, washed with hexane, and dried to give 2-(4'-chlorophenyl)-4-[4'-trifluoroacetylamino-methyl) phenyl]thiazole (1.56 g).mp.174–175° C.

¹H NMR (CDCl₃): δ 4.58 (d, 2 H), 6.58 (br s, 1 H), 7.30–7.48 (m, 4 H), 7.51 (s, 1 H), 7.91–8.05 (m, 4 H)

A solution of the above compound (0.59 g, 1.48 mmol) in DMF (5 mL) is added to a slurry of NaH (60%, 70 mg, 1.77 mmol) in DMF (2 mL) under nitrogen. The reaction mixture is stirred at room temperature until the gas evolution ceased (~1 h). n-Iodopentane (0.5 g, 2.5 mmol) is added, and the reaction mixture is heated at 100° C. (oil bath) for 3 h. The reaction mixture is cooled, poured into water (50 mL) and the organic material is extracted with EtOAc. The EtOAc layer is washed with brine, dried and stripped to yield a solid which is chromatographed (SiO₂, 0–5% MeOH/CH₂Cl₂) to give the desired compound (0.5 g).

¹H NMR (CDCl₃): δ 0.88 (t, 3H), 1.10–1.41 (m, 4H), 1.45–1.80 (m, 2H), 3.34 (t, 2H), 4.68 (d, 2H), 7.33 (d, 2H), 7.40–7.60 (m, 3H), 7.92–8.22 (m, 4H).

A solution of the above trifluoroacetylamide (1.05 g, 2.25 mmol) and aqueous KOH (25%, 6 mL, 2.68 mmol) in acetone (30 mL) is heated under reflux for 18 h. Acetone is distilled, and the residue is partitioned between water(15 mL) and EtOAc (25 mL). The organic layer is separated and the aqueous layer is extracted with EtOAc (3×20 mL). The combined organic extract is washed with brine, dried, and chromatographed (SiOC₂, 0–5% MeOH/CH₂Cl₂) to give the title compound (0.8 g), mp. 70–72° C.

¹H NMR (CDCl₃): 0.88 (t, 3 H), 1.12–1.45 (m, 4 H), 1.45–1.80 (m, 2 H), 2.64 (t, 2 H), 3.55(br s, 1 H), 3.85 (s, 2 H), 7.32–7.52 (m, 5 H), 7.83–8.13 (m, 4 H).

EXAMPLE 5a 2-(4'-Chlorophenyl-4-[[4'-(N-cyclopropyl, N-methyl)-aminomethyl]phenyl]thiazole (VI: $R_1$=H, $R_2$=4.Cl, $R_3$=c-propyl, $R_4$=Me)

Iodomethane (0.1 mL, 2.1 mmol) is added to a stirred mixture of 2-(4'-chlorophenyl-4-[[4'-(N-cyclopropyl) aminomethyl]phenyl]thiazole (prepared as in Example 5) (0.2 g, 0.6 mmol) and anhydrous K₂CO₃ (0.2 g, 1.4 mmol) in THF (15 mL). It is stirred for 16 h and filtered. The residue is washed with CH₂Cl₂, the washings and the filtrate are evaporated, and the residual oil is chromatographed (SiO₂, 0–2% MeOH/CH₂Cl₂) to give 50 mg of the title compound. Additional examples are shown in Table I, herein below.

EXAMPLE 6

(Process 6, Scheme 6)
2-(4'-Cyanophenyl-4-[[4'-(N,N-dimethyl)aminomethyl] phenyl]thiazole (VI: $R_1$=H, $R_2$=4.CN, $R_3$=$R_4$=Me)

To a mixture of 4'-methylacetophenone (30 g, 0.22 mol) and NBS (39.9 g, 0.22 mol) in CCl₄ (200 mL) is added 0.2 g of benzoylperoxide and the reaction mixture is heated under reflux for 6 h. Additional benzoylperoxide (0.2 g) is added and the mixture refluxed for 16 h. It is cooled and filtered. The filtrate is stripped to yield an oil (47.9 g). ¹H NMR indicates ~75% of the desired bromide which is used as is for the next step.

Dimethylamine (19% in EtOH, 21.2 g, 0.47 mol) is added dropwise to a solution of the above bromide (47.8 g, 0.22 mol) in CH₂Cl₂(100 mL) at 0° C. with stirring. After the addition is over the ice bath is removed, and the solution is stirred for 16 h at room temperature. The solvent is evaporated and the residue is taken up in CHCl₃. The chloroform solution is washed successively with saturated NaHCO₃, brine, dried and stripped. The residue is chromatographed (SiO₂, 2–10% MeOH/CH₂Cl₂) to give 15 g of 4'-(N,N-dimethylamino)methylacetphone. The amine is converted to the corresponding HCl salt.

Bromine (1.36 mL, 26.5 mmol) is added dropwise to a solution of the above HCl salt (5.6 g, 26.5 mmol) in CHCl₃ (60 mL) at 0° C. with stirring. The reaction mixture is stirred at room temperature for 2 h and the solvent evaporated yielding a brown solid (9 g).

¹H NMR (CDCl₃): δ 2.81 (s, 6 H), 4.26 (s, 2 H), 4.44 (s, 2 H), 7.89 (d, 2 H), 8.07 (d, 2 H).

A mixture of the above phenacyl bromide (1.54 g, 4.57 mmol) and 4-cyanothiobenzamide (0.74 g, 4.57 mmol) in EtOH (15 ml) is heated under reflux for 2 h. It is cooled and filtered to give a yellow solid (1.17 g). The solid is partitioned between CHCl₃ and saturated NaHCO₃ solution. The organic layer is separated, washed with brine, dried and evaporated to give 0.77 g of a solid. It is purified via column chromatography (SiO₂, 0–2% MeOH/CH₂Cl₂) to give 0.46 g of the title compound, mp. 121–122° C.

¹H NMR (CDCl₃): δ 2.37 (s, 6 H), 3.47 (s, 2 H), 7.42 (d, 2 H), 7.57 (s, 1 H), 7.77 (d, 2H), 7.92 (d, 2 H), 8.13 (d, 2 H).

EXAMPLE 6a 2-(4'-Fluorophenyl-4-[[[4'-(N,N-dimethyl)aminomethyl]-3 Õ-nitro]phenyl]thiazole(II: $R_1$=H, $R_2$=4.F, $R_3$=$R_4$=Me, $R_6$=H, $R_5$=3.NO₂, V=N, p=1)

Replacing 4'-methylacetophenone with 4'-methyl-3'-nitroacetophenone and following the above procedure the compound 4'-(N,N-dimethylamino)methyl-3'-nitroacetophenone is obtained. This is converted to the HCl salt and brominated to give α-bromo-4'-methyl-3'-nitroacetophenone.

A mixture of a-bromo-4'-(N,N-dimethylaminomethyl)-3'-nitroacetophenone (2.38 g, 6.23 mmol) and 4-fluorothiobenzamide (0.97 g, 6.23 mmol) in EtOH (150 mL) is heated under reflux for 6 h. EtOH is stripped and the residue is taken up in EtOAc. The EtOAc solution is washed successively with saturated Na₂CO₃ and brine, dried, and stripped. The residue is triturated with isopropyl alcohol and filtered to give 1.37 g of the title compound, mp. 112° C.

¹H NMR (CDCl₃): δ 2.25 (s, 6 H), 3.75 (s, 2 H), 7.17 (t, 2 H), 7.57 (s, 1 H), 7.69 (d, 1H), 7.98–8.18 (m, 3 H), 8.45 (d, 1 H),

EXAMPLE 6b 2-(4'-Fluorophenyl-4-[[[4'-(N,N-dimethyl)aminomethyl]-3'-amino]phenyl]thiazole (II: $R_1$=H, $R_2$=4.F, $R_3$=$R_4$=Me, $R_6$=H, $R_5$=NH₂, V=N, p=1)

A solution of the above nitro compound (Example 6a, 0.65 g) in EtOH (80 mL) and HCl (0.2 mL) is reduced under catalytic condition (5% Pd/C, 250 mg). After the reduction is complete (18 h) the catalyst is filtered and the filtrate is evaporated to dryness. The residue is partitioned between CH₂Cl₂ and saturated Na₂CO₃. The organic layer is washed with water, dried and stripped to give 0.47 g of the title compound, mp. 108–109° C.

¹H NMR (CDCl₃): δ 2.21 (s, 6 H), 3.45 (s, 2 H), 7.05 (t, 2 H), 7.14 (s, 1 H), 7.18–7.23 (d, 1 H), 7.31 (d, 1 H), 7.40 (s, 1 H), 7.97–8.08 (dd, 2 H).

EXAMPLE 6c 2-(4'-Fluorophenyl-4-[[[4'-(N,N-dimethyl)aminomethyl]-3'-acetylamino]phenyl]thiazole (II: $R_1$=H, $R_2$=4.F, $R_3$ =$R_4$= Me, $R_6$=H, $R_5$=NHCOCH₃, V=N, p=1)

Acetic anhydride (0.4 mL) is added to a solution of the above amine (Example 6b,0.47 g) in anhydrous THF (10 mL) and the solution is stirred at room temperature for 18 h. THF is evaporated and the residue is taken up in CHCl₃. The CHCl₃ solution is washed thoroughly with water, dried and stripped to yield a soft solid. It is triturated with ether and filtered to give 0.21 g of the title compound as a white solid, mp. 128.5° C.

¹H NMR (CDCl₃): δ 2.15 (s, 3 H), 2.30(s, 6 H), 3.50 (s, 2 H), 7.10–7.20 (m, 3 H), 7.50 (s, 1 H), 7.65–7.75 (d, 1 H), 8.00–8.10 (dd, 2 H), 8.80 (s, 1 H), 10.75 (br s, 1 H). Additional examples are shown in Table I, herein below.

EXAMPLE 7

(Process 7, Scheme 7)
2-(3'-Nitrophenyl-4-[[[4'-(N,N-dimethylamino)methyl]-3'-hydroxy]phenyl]thiazole (II: $R_1$=H, $R_2$=3.$NO_2$, $R_3$=$R_4$=$CH_3$, $R_5$=3.OH, $R_6$=H, V=N, p=1)

A mixture of 3-nitrobenzenethioamide (2.73 g, 15 mmol) and 3-methoxy-α-[bromoacetophenone (3.43 g, 15 mmol) in EtOH (30 mL) is heated under reflux for 18 h. It is cooled and filtered to give 4 g of 2-(3'-nitrophenyl)-4[(3'-methoxy)phenyl]thiazole as a yellow solid, mp. 122–123° C.

$^1$H NMR (CDCl$_3$): δ 3.94 (s, 3 H), 6.90–7.01 (dd, 1 H), 7.32–7.48 (t, 1 H), 7.50–7.75 (m, 4 H), 8.22–8.45 (dd,dd 2 H), 8.90 (dd, 1 H).

To an ice-cold solution of the above methylether (0.77 g, 2.46 mmol) in CH$_2$Cl$_2$ (10 mL) is added a solution of BBr$_3$ in CH$_2$Cl$_2$ (1M, 4.9 mL). The solution is stirred at 0° C. for 0.5 h and then at room temperature for 18 h. It is quenched with 12 mL of water, and the mixture is stirred for 0.5 h and filtered. The residue is washed thoroughly with water, followed by ether and dried to give 0.55 g of 2-(3'-nitrophenyl)-4[(3'-hydroxy)phenyl]thiazole.

A mixture of the above hydroxy compound (0.55 g, 1.93 mmol), p-formaldehyde (0.3 g), (Me)$_2$NH/EtOH (19%, 2.2 mL) in EtOH (7 mL) is refluxed for 8 h. EtOH is evaporated, and the residue is poured into water, and the solution is taken up in CH$_2$Cl$_2$. The organic layer is washed with brine, dried, stripped, and the residue chromatographed (SiO$_2$, MeOH/CH$_2$Cl$_2$ 2%) to yield 0.15 g of the title compound, mp. 157–160° C.

$^1$H NMR (CDCl$_3$): δ 2.32 (s, 6 H), 3.67 (s, 2 H), 7.00–7.01 (dd, 1 H), 7.40–7.48 (m, 2 H), 7.53 (s, 1 H), 7.65 (t, 1 H), 8.22–8.45 (dd,dd 2 H), 8.85 (m, 1 H).

Additional examples are shown in Table I, herein below.

EXAMPLE 8

(Process 8, Scheme 8)
5-(4'-Fluorophenyl)-3-[4"-(N-methyl-N-allylaminomethyl)-phenyl]-1,2,4-thiadiazole (III: $R^1$=H, $R^2$=4.F, $R^3$=$CH_3$, $R^4$=allyl, $R^5$=H, V=N, p=1)

To a solution of p-tolunitrile (10.1 g, 86.21 mmol) in 100 ml CHCl$_3$:MeOH (1:1) cooled to 5° C. in an ice-water bath is bubbled HCl for 1 hour to reach saturation. The solution is stirred at 10° C. for 43 hours, then concentrated under reduced pressure to yield p-methylbenzimidate hydrochloride as pale yellow crystals (15.98 g, 99%).

$^1$H NMR (CDCl$_3$): δ 2.44 (s, 3H), 4.52 (s, 3H), 7.36 (d, 2H), 8.29 (d, 2H).

To a solution of p-methylbenzimidate hydrochloride (8.00 g, 43.09 mmol) in MeOH (100 ml) is added NH$_3$/MeOH solution (2.68M, 24.12 ml, 64.64 mmol). Upon the addition of the NH$_3$, the mixture has a pH around 8.5. To this solution is added ammonium chloride (2.30 g, 43.09 mmol). The reaction mixture is stirred at room temperature for 20 hours, then cooled in refrigerator and the precipitate is removed by filtration. The mother liquor is concentrated to yield the crude product which is taken up in a limited amount of cold EtOH and the white precipitate is filtered. The beige filtrate is concentrated to yield p-methylbenzamidine hydrochloride as an off-white solid (7.15 g, 97%).

$^1$H NMR (DMSO$_{d6}$): δ 2.41 (s, 3H), 7.43 (d, 2H), 7.78 (d, 2H), 9.24–9.39 (broad d, 3H).

To a mixture of p-methylbenzamidine hydrochloride (5.1 g, 30.0 mmol) in CHCl$_3$ (100 ml) is added triethyl amine (15.12 g, 20.9 ml, 150.0 mmol) and cooled to 5° C. in an ice-water bath. To the mixture is slowly added perchlorom-ethyl mercaptan (95%, 6.16 g, 31.5 mmol) in CHCl$_3$(10 ml) over 1 hour. The yellow solution is allowed to warm up to room temperature. After 2 hours the mixture is washed with water (100 ml×2) and brine (100 ml). The organic layer is dried over MgSO$_4$ and the solvent is removed under reduced pressure to yield a brown oil. The oil is purified on a bed of silica gel, eluting with 1:1 CHCl$_3$:hexanes to yield 3-(p-tolyl)-5-chloro-1,2,4-thiadiazole as a yellow solid (2.78 g, 44%).

$^1$H NMR (CDCl$_3$): δ 2.41 (s, 3H), 7.30(d, 2H), 8.13 (d, 2H).

A mixture of 3-(p-tolyl)-5-chloro-1,2,4-thiadiazole (0.50 g, 2.37 mmol) and [1,3-bis(diphenylphosphino)propane] nickel(II) chloride catalyst (1.41 g, 2.61 mmol) in anhydrous THF (20 ml) is cooled in an ice-water bath. To this mixture is added slowly 4-fluorophenyl-magnesium bromide (1.0M in THF, 2.5 ml, 2.49 mmol) with exclusion of both moisture and oxygen. The mixture is allowed to warm to room temperature and stirred for 13 hours under N$_2$. The mixture is filtered through celite and concentrated. The residue is taken up in CHCl$_3$ (50 ml) and washed with brine (50 ml×2). The organic layer is dried over magnesium sulfate and concentrated. The residue is purified on a silica gel column, eluting with 3:7 CHCl$_3$:hexanes to yield 5-(4'-fluorophenyl)-3-(p-tolyl)-1,2,4-thiadiazole (0.20 g, 31%).

$^1$H NMR (CDCl$_3$): δ 2.43 (s, 3H), 7.21–7.32 (m, 4H), 8.06 (m, 2H), 3.24 (d, 2H).

To a solution of 5-(4'-fluorophenyl)-3-(p-tolyl)-1,2,4-thiadiazole (0.16 g, 0.59 mmol) in CCl$_4$ (20 ml) is added NBS (0.11 g, 0.59 mmol) and the mixture is heated to reflux for 36 hours The mixture is cooled to room temperature and filtered through celite. The mother liquor is concentrated. The residue is taken up in chloroform (30 ml) and washed with water (30 ml). The organic layer is dried over MgSO$_4$ and concentrated to yield 5-(4'-fluorophenyl)-3-(p-bromomethylphenyl)-1,2,4-thiadiazole, (0.22 g) as crude product which is used as is without further purification.

$^1$H NMR (CDCl$_3$): δ 4.55 (s, 2H), 7.19 (d, 2H), 7.54 (d, 2H), 8.06 (m, 2H), 8.35 (d, 2H).

To a solution of 5-(4-fluorophenyl)-3-(4-bromomethylphenyl)-1,2,4-thiadiazole (0.19 g, 0.54 mmol) in chloroform (15 ml) is added slowly N-methyl-allylamine (0.14 g, 1.62 mmol) in chloroform (5 ml). The solution is stirred at room temperature for 12 hours and washed with water (30 ml). The organic layer is dried over K$_2$CO$_3$ and concentrated. The resulting oil is chromatographed on a silica gel column, eluting with ethyl acetate:hexanes (30:60) to yield the title compound as an oil. (0.10 g, 55%).

$^1$H NMR (CDCl$_3$): δ 2.23 (s, 3H), 3.05 (d, 2H), 3.57 (s, 2H), 5.12–5.30 (m, 2H), 5.85–6.05 (m, 1H), 7.19 (d, 2H), 7.45 (d, 2H), 8.07 (m, 2H), 8.32 (d, 2H).

Additional examples are shown in Table I, herein below.

EXAMPLE 9

(Process 9, Scheme 9)
1,3,4-Thiadiazoles and 1,3,4-Oxadiazoles
2-(3'-Nitrophenyl)-5-(4"-(N,N-dimethylaminomethyl)phenyl]-1,3,4-thiadiazole (IV: $R^1$=H, $R^2$=3.$NO_2$, $R^3$=$R^4$=$CH_3$, $R^5$=H, V=N, p=1)

To a solution of 3-nitrobenzhydrazide (2.16 g, 11.92 mmol) in pyridine (40 ml) cooled to 0° C. in an ice bath is added dropwise p-toluoyl chloride (1.94 g, 11.92 mmol). The mixture is allowed to warm to room temperature and stirred for 12 hours. The mixture is quenched with 350 mL of water and stirred for thirty minutes. The precipitate is filtered and dried in a vacuum oven to yield 1-[(4-methyl)benzoyl]-2-(3-nitrobenzoyl)hydrazine as a pale yellow solid. (2.94 g, 82%).

¹H NMR(DMSO_d6): δ 2.40 (s, 3H), 7.35 (d, 2H), 7.86 (d, 2H), 7.87 (t, 1H), 8.37 (d, 1H), 8.45 (d, 1H), 8.76 (s, 1H), 10.58 (s, 1H), 10.90 (s, 1H).

A mixture of 1-[(4-methyl)benzoyl]-2-(3-nitrobenzoyl) hydrazine (1.40 g, 4.68 mmol) and Lawesson's Reagent (0.95 g, 2.34 mmol) in benzene (25 ml) is slowly heated to 60° C. After 3 hours the solution is concentrated, quenched with 35 ml of water and heated to reflux for 12 hours. The mixture is then cooled to room temperature and the precpitate is collected by filtration. The precipitate is then taken up in chloroform (100 ml) and the insoluble portion is removed by filtration. The filtrate is then dried over MgSO_4 and concentrated to yield 2-(3'-nitrophenyl)-5-(p-tolyl)-1,3,4-thiadiazole as a pale yellow solid. (0.67 g, 48%).

¹H NMR(CDCl_3): δ 2.45 (s, 3H), 7.35 (d, 2H), 7.73 (t, 1H) 7.92 (d, 2H), 8.38 (t, 2H), 8.81 (s, 1H).

To a solution of 2-(3'-nitrophenyl)-5-(p-tolyl)-1,3,4-thiadiazole (0.66 g, 2.22 mmol) in CCl_4 (75 ml) is added NBS (0.43 g, 2.44 mmol) and refluxed for 12 hours. The mixture is then concentrated and the residue is taken up In chloroform (50 ml) and washed with saturated NaHCO_3 (50 ml) and brine (50 ml). The organic layer is dried over MgSO_4 and concentrated to yield 2-(3'-nitrophenyl)-5-(p-bromomethylphenyl)-1,3,4-thiadiazole as a tan solid. (0.69 g, 83%).

¹H NMR (CDCl_3): δ 4.51 (s, 2H), 7.55 (d, 2H), 7.72 (t, 1H), 8.01 (d, 2H), 8.39 (t, 2H), 8.80 (s, 1H).

To a suspension of 2-(3'-nitrophenyl)-5-(p-bromomethylphenyl)-1,3,4-thiadiazole (0.69 g, 1.83 mmol) in warm EtOH (25 ml) is added excess dimethyl amine/ EtOH solution (~19% w/w, 3 ml) and stirred at room temperature. After 12 hours the solution is concentrated and the residue is taken up in chloroform (50 ml) and washed with saturated NaHCO_3 (50 ml) and brine (50 ml). The organic layer is dried over K_2CO_3 and concentrated to yield a brown solid which is chromatographed on a silica gel column, eluting with 10% MeOH/CHCl_3 to yield the title compound as a tan solid. (0.26 g, 37%).

¹H NMR (CDCl_3): δ 2.29 (s, 6H), 3.50 (s, 2H), 7.50 (d, 2H), 7.72 (t, 1H), 7.97 (d, 2H), 8.39 (t, 2H), 8.82 (s, 1H).

EXAMPLE 9a 2-(3'-Nitrophenyl)-5-[4"-(N,N-dimethylaminomethyl) phenyl]-1,3,4-oxadiazole (V: $R^1$=H, $R^2$=3.NO_2, $R^3$=$R^4$=CH_3, $R^5$=H, V=N, p=1)

A suspension of 1-[(4-methyl)benzoyl)]-2-(3-nitrobenzoyl)hydrazine (1.37 g, 4.58 mmol) in 20 ml thionyl chloride is heated to reflux for 12 hours. The solution is concentrated and the residue is taken up in chloroform (50 ml) and washed with water (50 ml) and brine (50 ml). The organic layer is dried over MgSO_4 and concentrated to yield 2-(3'-nitrophenyl)-5-(p-tolyl)-1,3,4-oxadiazole as a yellow solid. (1.12 g, 87%).

¹H NMR (CDCl_3): δ 2.47 (s, 3H), 7.39 (d, 2H), 7.76 (t, 1H), 8.07 (d, 2H), 8.42 (d, 1H), 8.80 (d, 1H), 8.95 (s, 1H).

To a solution of 2-(3'-nitrophenyl)-5-(p-tolyl)-1,3,4-oxadiazole (1.00 g, 3.56 mmol) in CCl_4 (25 ml) is added NBS (0.43 g, 3.74 mmol) and the mixture is heated to reflux. After 24 hours the solution is concentrated and the residue taken up in chloroform (100 m) and washed with saturated NaHCO_3 (50 ml) and brine (50 ml). The organic layer is dried over MgSO_4 and concentrated to yield 2-(3'-nitrophenyl)-5-[(p-bromomethyl)phenyl]-1,3,4-oxadiazole as a tan solid. (0.69 g, 83%).

¹H NMR (CDCl_3): δ 4.55 (s, 2H), 7.59 (d, 2H), 7.78 (t, 1H), 8.16 (d, 2H), 8.45 (d, 1H), 8.52 (d, 1H), 8.96 (s, 1H).

To a suspension of 2-(3'-nitrophenyl)-5-[(p-bromomethyl)phenyl]-1,3,4-oxadiazole (0.50 g, 1.39 mmol) in warm EtOH (25 ml) is added excess dimethyl amine/ EtOH solution (~19% w/w, 3 ml) and stirred at room temperature for 12 hours. The solution is then concentrated and the residue taken up in chloroform (30 ml) and is washed with saturated NaHCO_3 (30 ml) and brine (30 ml). The organic layer is dried over K_2CO_3 and concentrated to yield a brown oil which is chromatographed on a silica gel column eluting with 10% MeOH/CHCl_3 to yield the title compound as a tan solid. (0.22 g, 49%).

¹H NMR (CDCl_3): δ 2.25 (s, 6H), 3.52 (s, 2H), 7.54 (d, 2H), 7.77 (t, 1H), 8.12 (d, 2H), 8.40 (d, 1H), 8.54 (d, 1H), 8.95 (s, 1H).

By following the process schemes described in the preceding Examples the following compounds have also been prepared.

TABLE I

| Example | Process Scheme | Name |
|---------|----------------|------|
| 1d | 1 | 2-(4'-fluorophenyl)-4-[4"-(N-methyl-N-(2-furfuryl)aminomethyl)phenyl]thiazole |
| 1e | 1 | 2-(4'-fluorophenyl)-4-[4"-(3-butyn-1-oxymethyl)phenyl]thiazole |
| 1f | 1 | 2(4'-fluorophenyl)-4-(4"-(N-methyl-N-propargylaminomethyl)phenyl]thiazole |
| 1g | 1 | 2-(4'-chlorophenyl)-4-[4"-(N-methyl-N-allylaminomethyl)phenyl]thiazole |
| 1h | 1 | 2-(4'-nitrophenyl)-4-[4"-(N-methyl-N-allylaminomethyl)phenyl]thiazole |
| 1i | 1 | 2-(4'-flurophenyl)-4-[4"-(2-(t-butoxy)ethoxymethyl)phenyl]thiazole |
| 1j | 1 | 2-(2'-nitrophenyl)-4-[4"-(N-methyl-N-allylaminomethyl)phenyl]thiazole |
| 1k | 1 | 2-(3'-nitrophenyl)-4-[4"-(N-methyl-N-allylaminomethyl)phenyl]thiazole |
| 1l | 1 | 2-(4'-fluorophenyl)-4-[4"-(2-propenyloxymethyl)phenyl]thiazole |
| 1m | 1 | 2-(4'-fluorophenyl)-4-[4"-(N-cyclopropylaminomethyl)phenyl]thiazole |
| 1n | 1 | 2-(4'-fluorophenyl)-4-[4"-(N-allylaminomethyl)phenyl]thiazole |
| 1o | 1 | 2-(4'-nitrophenyl)-4-[4"-(N-methyl-N-propylaminomethyl)phenyl]thiazole |
| 1p | 1 | 5-bromo-2-(4'-nitrophenyl)-4-[4"-(N-methyl-N-allyl-aminomethyl)phenyl]thiazole |
| 1q | 1 | 2-(4'-(1H-pyrrol-1-yl)phenyl]-4-[4"-(N-methyl-N-propylmethyl)phenyl]thiazole |
| 1r | 1 | 2-(4'-aminophenyl)-4-[4"-(N-methyl-N-propylmethyl)phenyl]thiazole |
| 1s | 1 | 2-(4'-nitrophenyl)-4-[4"-(diallylaminomethyl)phenyl]thiazole |
| 1t | 1 | 2-(4'-nitrophenyl)-4-[4"-(dipropylaminomethyl)phenyl]-thiazole |
| 6d | 6 | 2-(4'-trifluoromethylphenyl)-4-[4"-(N-methyl-N-allylamino-methyl)phenyl]thiazole |
| 2c | 2 | 2-(4'-pyridyl)-4-[4"-(N-methyl-N-propylaminomethyl)phenyl]thiazole |
| 6e | 6 | 2-(4'-cyanophenyl)-4-[4"-(N-methyl-N-propylaminomethyl)phenyl]-thiazole |
| 1u | 1 | 2-(4'-chlorophenyl)-4-[4"-(N-methyl-N-(2-dimethylaminoethyl)aminomethyl)-phenyl]thiazole |
| 6f | 6 | 2-(2'-fluoro-4'-trifluoromethylphenyl)-4-[4"-(N-methyl-N-propylamino-methyl)phenyl]thiazole |
| 1v | 1 | 2-(4'-nitrophenyl)-4-[4"-(diisopropylaminomethyl)-phenyl]thiazole |
| 1x | 1 | 2-(4'-nitrophenyl)-4-[4"-(dimethylaminomethyl)phenyl]thiazole |

TABLE I-continued

| Example | Process Scheme | Name |
|---|---|---|
| 1y | 1 | 2-(2'-fluorophenyl)-4-(4"-(N-methyl-N-allylaminomethyl)phenyl]thiazole |
| 1z | 1 | 2-(4'-trifluoromethoxyphenyl)-4-[4"-(N-methyl-N-allylaminomethyl)-phenyl]thiazole |
| 1aa | 1 | 2-(3'-nitrophenyl)-4-[4"-(dimethylaminomethyl)phenyl]-thiazole |
| 1bb | 1 | 2-(3'-nitrophenyl)-4-[4"-(N-methyl-N-propylaminomethyl)phenyl]thiazole |
| 1cc | 1 | 2-(4'-nitrophenyl)-(4-[4"-[(2-diethylaminoethoxy)-methyl]phenyl]thiazole |
| 1dd | 1 | 2-(3'-nitrophenyl)-4-[4"-(N-methyl-N-(2-methoxyethyl)aminomethyl)-phenyl]thiazole |
| 6g | 6 | 2(4'-iodophenyl)-4-[4"-(N-methyl-N-propylaminomethyl)phenyl]-thiazole |
| 1ee | 1 | 2-(4'-chlorophenyl)-4-[4"-(N-methyl-N-(2-hydroxyethyl)aminomethyl)-phenyl]thiazole |
| 6h | 6 | 4-(4'-N-methyl-N-propylamino-methyl)phenyl]-2-(pyrid-3"-yl)thiazole |
| 1ss | 1 | 2-(4'-chlorophenyl)-4-[4"-[[2-(diethylamino)ethyl]-thiomethyl]phenyl]thiazole |
| 6i | 6 | 2-[4'-(trimethylsilylethynyl)phenyl]-4-[4"-(N-methyl-N-propylamino-methyl)phenyl]thiazole |
| 6j | 6 | 2-(4'-ethynylphenyl)-4-[4"-N-methyl-N-propylaminomethyl)phenyl]thiazole |
| 1ff | 1 | 2-(4'-chlorophenyl)-4-[4"-[(4-ethylpiperzin-1-yl)methyl]-phenyl]thiazole |
| 6k | 6 | 2-(4'-methoxy-3'-nitrophenyl)-4-[4"-(N-methyl-N-propylamino-methyl)phenyl]thiazole |
| 6l | 6 | 2-(4'-methoxy-3'-nitrophenyl)-4-[4"-(dimethylaminomethyl)phenyl]thiazole |
| 1gg | 1 | 2-(4'-chlorophenyl)-4-[4"-[[3(dimethylamino)propyl]aminomethyl]-phenyl]thiazole |
| 1hh | 1 | 2-(3'-nitrophenyl)-4-[4"-(N-hydroxymethylaminomethyl)-phenyl]thiazole |
| 1ii | 1 | 2-(3'-nitrophenyl)-4-[4"-(N-methyl-N-(2-phenylethyl)aminomethyl)-phenyl]thiazole |
| 8a | 8 | 5-(4'-fluorophenyl)-3-[4"-(N-methyl-N-allylaminomethyl)phenyl]-1,2,4-thiadiazole |
| 8b | 8 | 5-phenyl-3-[4"-(N-methyl-N-allylaminomethyl)phenyl]-1,2,4-thiadiazole |
| 1tt | 1 | 2-(4'-chlorophenyl)-4-[4"-(N-methyl-(2-N-methylaminoethyl)-amino-methyl)phenyl]thiazole |
| 5c | 5 | 2-(4'-chlorophenyl)-4-[4"-(N-octylaminoethyl)amino-methyl)phenyl]thiazole |
| 6n | 6 | 2-(3'-cyanophenyl)-4-[4"-(N-methyl-N-propylaminomethyl))phenyl]thiazole |
| 6o | 6 | 2-(3'-cyanophenyl)-4-[4"-(dimethylaminomethyl)phenyl]thiazole |
| 6u | 6 | 2-(6"-chloropyrid-3"-yl)-4-[4'-(N-allyl-N-methyl-aminomethyl)phenyl]thiazole |
| 8c | 8 | 5-(4'-methoxyphenyl)-3-[4"-(N-methyl-N-allylaminomethyl)phenyl]-1,2,4-thiadiazole |
| 6p | 6 | 2-(4'-methyl-3'-nitrophenyl)-4-[4"-(N-methyl-N-propylaminomethyl)-phenyl]thiazole |
| 1jj | 1 | 2-(4'-chlorophenyl)-4-[4"-(N-(2-dimethylaminoethyl)aminomethyl)phenyl]thiazole |
| 5d | 5 | 2-(3'-nitrophenyl)-4-[amidinothiomethyl)phenyl]thiazole |
| 5e | 5 | 2-(4'-chlorophenyl)-4-{4-[α-((2-dimethylaminoethyl)amino)acetyl-aminomethyl]phenyl}thiazole |
| 1kk | 1 | 2-(4'-methoxy-3'-nitrophenyl)-4-[4"-(N-methyl-N-allylamino-methyl)phenyl]thiazole |
| 9b | 9 | 2-(3'-nitrophenyl)-5-(4"-(N-methyl-N-allylaminomethyl)-1,3,4-oxadiazole |
| 9d | 9 | 2-(3'-nitrophenyl)-5-[4"-(N-methyl-N-allylaminomethyl)-1,3,4-thiadiazole |
| 1ll | 1 | 2-(4'-methoxy-3'-nitrophenyl)-4-[4"-(N-methyl-N-(2-hydroxy-ethyl)amino-methyl)phenyl]thiazole |
| 6q | 6 | 2-(2'-fluoro-4'-trifluoromethylphenyl)-4-[4"-(di-methyl-aminomethyl)phenyl]thiazole |
| 8d | 8 | 5-(4'-methoxyphenyl)-3-4[4"-(dimethylaminomethyl)phenyl]-1,2,4-thiadiazole |
| 8e | 8 | 5-(4'-methoxyphenyl)-3-[4"-((2-dimethylaminoethyl)thiomethyl)phenyl]-1,2,4-thiadiazole |
| 5f | 5 | 2-(4'-bromophenyl)-4-[4,'-aminomethylphenyl]thiazole |
| 1mm | 1 | 2-(4'-methoxy-3'-nitrophenyl)-4-[4"-(N-methyl-N-(2-methylaminoethyl)amino-methyl)phenyl]thiazole |
| 9f | 9 | 2-(4'-chlorophenyl)-5-[4"-(dimethylaminomethyl)phenyl]-1,3,4-oxadiazole |
| 9g | 9 | 2-(4'-chlorophenyl)-5-[4"-(dimethylaminomethyl)phenyl]-1,3,4-thiadiazole |
| 9h | 9 | 2-(4'-chlorophenyl)-5-[4"-(N-methyl-N-allylaminomethyl)phenyl]-1,3,4-thiadiazole |
| 9i | 9 | 2-(4'-chlorophenyl)-5-[4"-(N-methyl-N-allylaminomethyl)phenyl]-1,3,4-oxadiazole |
| 1nn | 1 | 2-(3'nitro-4'-methoxyphenyl)-4-[4"[(2-diethylaminoethylthio)methyl]phenyl]thi-azole |
| 1oo | 1 | 2-(3',4'-dimethoxyphenyl)-4-[4"-(dimethylaminomethyl)phenyl]thiazole |
| 9j | 9 | 2-(4'-methoxyphenyl)-5-[4"-(dimethylaminomethyl)phenyl]-1,3,4-oxadiazole |
| 9k | 9 | 2-(4'-methoxyphenyl)-5-[4"-(N-methyl-N-allylaminomethyl)phenyl]-1,3,4-oxadiazole |
| 1pp | 1 | 2-(3'-nitrophenyl)-4-[4"-[(2-dimethylaminoethyl-thio)methyl]phenyl]thiazole |
| 6t | 6 | 2-(4'-fluorophenyl)-4-[3'-acetamido-4"-(dimethylaminomethyl)phenyl]-thiazole |
| 1qq | 1 | 2-(4'-chlorophenyl)-4-[4"-[(4-methylpiperazin-1-yl)methyl]phenyl]thiazole |
| 1rr | 1 | 2-(4'-chlorophenyl)-4-[4"-[(2-dimethylaminoethyl-thio)methyl]phenyl]thiazole |
| 7b | 7 | 2-(3'-nitrophenyl)-4-[3"-hydroxyl-4"-(N-methylpiperazino)-methylphenyl]-thiazole |
| 3a | 3 | 2-(4'-fluorophenyl)-4-[4"-(2-dimethylaminoethyl)phenyl]thiazole |
| 3b | 3 | 2-(3'-nitrophenyl)-4-[4"-(2-dimethylaminoethyl)phenyl]thiazole |

TABLE I-continued

| Example | Process Scheme | Name |
|---|---|---|
| 3d | 3 | 2-(4'-methoxyphenyl)-4-[4"-[2-(N-allyl-N-methylamino)ethyl]phenyl]-thiazole |
| 3e | 3 | 2-(4-'methoxyphenyl)-4-[4"-(2-(N-methylpiperazino)ethyl]phenyl]thiazole |
| 9l | 9 | 2-(3'-nitrophenyl)-5-[4"-(thiomorpholinomethyl)phenyl]-1,3,4-thiadiazole |
| 4a | 4 | 2-(4'-fluorophenyl)-4-(4"-(3-dimethylaminopropynyl)phenyl]thiazole |
| 4b | 4 | 2-(4'-methoxyphenyl)-4-[4"-(3-dimethylaminopropynyl)phenyl]thiazole |
| 4d | 4 | 2-(4'-methoxyphenyl)-4-[4"-(3-dimethylaminopropyl)phenyl]thiazole |

Organisms:

Three strains of Candida (*Candida parpsilosis, Candida tropicalis, Candida albicans*-ATCC 36082) as well as *Cryptococcus neoformans* were used for the initial testing, Active compounds were then tested against fluconazole resistant *Candida albicans, Candida krusei, Torulopsis glabrata*, and *Cryptococcus neoformans* along with *Sporothrix shenkii* and *Aspergillus flavus* in the secondary round of testing. All clinical strains used in this study were blood culture isolates from the Clinical Microbiology Laboratory of Harbor-UCLA Medical Center, Torrance, Calif. The organisms were maintained on Sabourahd Dextrose Agar slants at 4° C. For experimentation, singlet suspensions of each organism were prepared by growing the yeast overnight at 27° C. on a rotating drum in yeast-nitrogen base broth (YNB) with amino acids (Difco, Detroit, Mich.), pH 7.0 with 0.05M morpholinepropanesulfonic acid (MOPS). The suspension was then centrifuged and washed twice with 0.85% NaCl. This was followed by sonication of the washed cell suspension for 4s (Branson Sonifier, model 350, Danbury, Conn.). The singlet blastospores were counted in a hemocytometer and adjusted to the desired concentration in 0.85% NaCl.

Antifungal Activity:

The antifungal activity of the compounds and Fluconazole against the Candida and Cryptococcus strains were determined using a modification of a broth microdilution technique. Test compounds were diluted in DMSO to a 1.0 mg/ml ratio then diluted to 64 µg/ml in YNB broth, pH 7.0 with MOPS (Fluconazole was used as the control). This was to provide a working solution of each compound. Using a 96-well plate, wells 1 and 3 through 12 were prepared with YNB broth, ten fold dilutions of the compound solution were made in wells 2 through 11 (concentration ranges were 64 to 0.125 µg/ml). Well one served as a sterility control and blank for the spectrophotometric assays. Well twelve served as a growth control. The microtiter plates were inoculated with 10 ul in each of well 2 through 11 (final inoculum size was $10^4$ organisms/ml). Inoculated plates were incubated for 48 hrs., at 35° C. The MIC values were determined spectrophotometrically by measuring the absorbance at 420 nm (Automatic Microplate Reader, DuPont Instruments, Wilmington, Del.) after agitation of the plates for 2 min with a vortex-mixer (Vorte-Genie 2 Mixer, Scientific Industries, Inc., Bolemia, N.Y.). The MIC endpoint was defined as the lowest drug concentration exhibiting approximately 50% (or more) reduction of the growth compared with the control well. With the turbidity assay this was defined as the lowest drug concentration at which turbidity in the well was <50% of the control ($IC_{50}$). Minimal Cytolytic Concentrations (MCC) were determined by subculturing all wells from the 96-well plate onto a Sabourahd Dextrose Agar (SDA) plate and incubated for 1 to 2 days at 35° C. and the viability was checked.

The following Table II demonstrates the antifungal activities of a selected number of examples.

TABLE II

| Example # | C. albicans MIC[a] | C. albicans MCC[b] | C. parapsilosis MIC | C. parapsilosis MCC | C. tropicalis MIC | C. tropicalis MCC | Crtpto. neoformans MIC | Crtpto. neoformans MCC |
|---|---|---|---|---|---|---|---|---|
| 1h | 0.5[c] | 2 | 0.25 | 1 | 0.125 | 0.5 | 0.5 | 2 |
| 1k | 0.5 | 1 | 0.25 | 0.5 | 0.25 | 0.25 | 0.25 | 0.5 |
| 1o | 1 | 4 | 1 | 4 | 2 | 32 | 0.125 | 2 |
| 1x | 1 | 2 | 1 | 2 | 1 | 2 | 2 | 2 |
| 5b | 1 | 4 | 1 | 4 | 1 | 4 | 1 | 4 |
| 6k | 1 | 2 | 0.5 | 2 | 1 | 2 | 1 | 1 |
| 6l | 0.5 | 1 | 0.25 | 0.5 | 0.25 | 1 | 0.25 | 0.5 |
| 1gg | 1 | 2 | 1 | 4 | 1 | 2 | 1 | 2 |
| 6p | 1 | 8 | 1 | 4 | 2 | 16 | 1 | 4 |
| 1kk | 1 | 2 | 0.25 | 1 | 1 | 2 | 0.5 | 2 |
| 9c | 1 | 4 | 1 | 1 | 1 | 1 | 2 | 4 |
| 7a | 1 | 4 | 1 | 0.25 | 1 | 2 | 1 | 4 |
| 1 | 4[c] | 16 | 4 | 16 | 4 | 16 | 4 | 16 |
| 1g | 2 | 8 | 4 | 8 | 2 | 8 | 2 | 8 |
| 1n | 8 | 16 | 4 | 8 | 8 | 16 | 8 | 8 |
| 2b | 4 | 16 | 2 | 16 | 4 | 16 | 4 | 16 |
| 6e | 4 | 4 | 2 | 4 | 2 | 16 | 0.5 | 1 |
| 1u | 8 | 8 | 4 | 4 | 4 | 4 | 4 | 4 |
| 6f | 8 | 16 | 4 | 8 | 2 | 8 | 4 | 8 |
| 1aa | 4 | 4 | 4 | 4 | 4 | 4 | 4 | 4 |
| 1ee | 4 | 16 | 2 | 16 | 4 | 8 | 2 | 16 |
| 6m | 4 | 8 | 4 | 4 | 4 | 8 | 4 | 4 |
| 1tt | 4 | 16 | 4 | 16 | 2 | 16 | 2 | 4 |
| 6o | 2 | 4 | 2 | 8 | 2 | >64 | 8 | 16 |
| 1jj | 8 | 8 | 4 | 4 | 4 | 4 | 8 | 8 |
| 1ll | 8 | 8 | 2 | 2 | 4 | 4 | 2 | 8 |
| 6g | 8 | 4 | 4 | 2 | 8 | 4 | | 8 |
| 9j | 4 | 32 | 8 | 8 | 0.5 | 0.5 | 0.25 | 8 |
| 1gg | 4 | 8 | 4 | 8 | 4 | 8 | 4 | 8 |
| 1rr | 4 | 8 | 4 | 8 | 4 | 8 | 4 | 8 |
| Flucona-zole | 0.25 | >64 | 0.5 | >64 | 0.25 | >64 | 1.0 | >64 |
| | 0.5 | >64 | 1.0 | >64 | 1.0 | >64 | 0.5 | >64 |
| Amp-B | 0.25 | | 0.25 | | | | <0.03 | |
| Naftifine | 32 | | | | | | 4.0 | | a. MIC = Minimum inhibitory concentration (50% Inhibition)
b. MCC = Minimum cytolytic concentration
c. All values are given µg/ml

What is claimed is:

1. A compound of the formula:

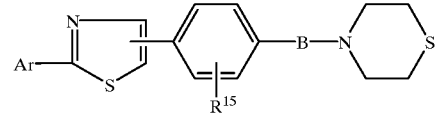

wherein

Ar is selected from among pyridyl, halo substituted pyridyl and

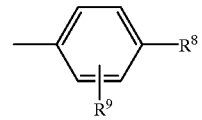

where $R^8$ is hydrogen, halo, nitro, amino, trifluoromethoxy, pyrrolyl, lower alkoxy, trifluoromethyl, cyano, lower alkynyl or trimethylsilyl lower alkynyl, and $R^9$ is hydrogen, nitro, lower alkoxy or cyano;

B is lower alkylene or lower alkynylene; and $R^{15}$ is hydrogen, nitro, amino, lower alkanamido or hydroxy; or a nontoxic pharmacologically acceptable salt thereof.

2. A compound according to claim 1 of the formula:

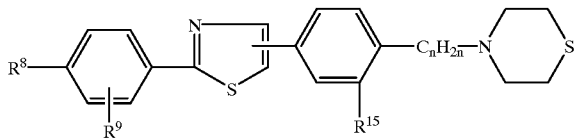

wherein:

$R^8$ is hydrogen, halo, nitro, amino, trifluoromethoxy, pyrrolyl, lower alkoxy, trifluoromethyl, cyano, lower alkynyl or trimethylsilyl lower alkynyl; and $R^9$ is hydrogen, nitro, lower alkoxy or cyano; and $R^{15}$ is hydrogen, nitro, amino, lower alkanamido or hydroxy; and n is an integer having a value of 1 to 3; or a nontoxic pharmacologically acceptable salt thereof.

3. A compound according to claim 1 of the formula:

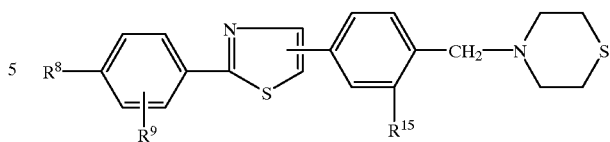

wherein:

$R^8$ is hydrogen, halo, nitro, lower alkoxy, cyano, trifluoromethyl or lower alkyl;

$R^9$ is hydrogen, nitro, halogen or cyano; and $R^{15}$ is hydrogen or hydroxy; or a nontoxic pharmacologically acceptable salt thereof.

4. A pharmaceutical composition comprising an effective amount of a compound of claim 1 in combination with a pharmaceutically acceptable carrier.

5. A method for treating a fungal infection which comprises administering to a mammalian host an effective amount of the compound of claim 1 in unit dosage form.

* * * * *